United States Patent
Dhainaut et al.

Patent Number: 5,877,190
Date of Patent: Mar. 2, 1999

[54] SUBSTITUTED BIPHENYL COMPOUNDS

[75] Inventors: Alain Dhainaut, Chatou; Guillaume Poissonnet, villebon-sur-Yvette; Emmanuel Canft, Paris; Michel Lonchampt, chevilly-La-Rue, all of France

[73] Assignee: Adir et Compagnie, Courbevoie, France

[21] Appl. No.: 943,562

[22] Filed: Oct. 3, 1997

[30] Foreign Application Priority Data

Apr. 10, 1996 [FR] France ................... 96.12111

[51] Int. Cl.$^6$ ............. C07D 401/02; C07D 307/79; A61K 31/34

[52] U.S. Cl. ............. 514/337; 514/357; 514/640; 546/276.7; 546/280.4; 546/284.1; 546/329; 564/253

[58] Field of Search ............. 564/253; 514/640, 514/337, 357; 546/276.7, 280.4, 284.1, 329

[56] References Cited

U.S. PATENT DOCUMENTS

| | | | |
|---|---|---|---|
| 3,864,146 | 2/1975 | Oda et al. | 503/210 |
| 4,829,075 | 5/1989 | Ehrhardt et al. | 514/340 |

FOREIGN PATENT DOCUMENTS

| | | |
|---|---|---|
| 2142470 | 1/1973 | France . |
| WO96/03396 | 2/1996 | WIPO . |

*Primary Examiner*—Zinna Northington Davis
*Attorney, Agent, or Firm*—The Firm of Gordon W. Hueschen

[57] ABSTRACT

A compound of formula (I):

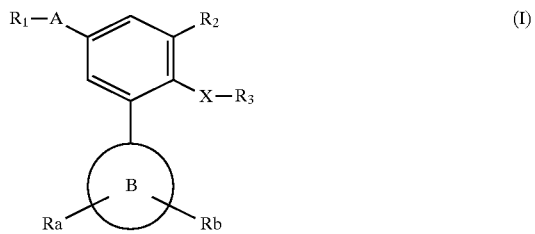

wherein:
  $R_1$ represents unsubstituted or substituted cycloalkyl, phenyl, naphthyl, heterocyclic, alkyl or alkenyl,
  A represents a bond, oxygen, sulphur, a group

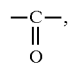

a group

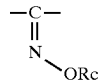

or a group

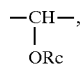

wherein Rc represents hydrogen, alkyl or cycloalkyl, $R_2$ represents halogen, substituted or unsubstituted alkyl, substituted or unsubstituted alkenyl, substituted or unsubstituted alkynyl, cycloalkyl, formyl, carboxy, alkylcarbonyl, cycloalkylcarbonyl, alkoxycarbonyl, cycloalkyloxycarbonyl, optionally substituted carbamoyl, optionally substituted amino, formylamino, cyano, optionally substituted amidino, hydroxyaminomethyl, amide oxime, hydrazono, or a group selected from:

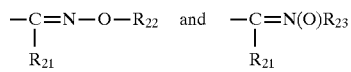

wherein $R_{21}$, $R_{22}$ and $R_{23}$ are as defined in the description, $R_3$ represents hydrogen or alkyl, cycloalkyl or acyl, or

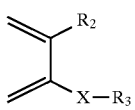

together form the ring

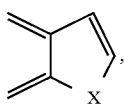

X is oxygen, sulphur, or NR", B is phenyl, Ra and Rb, which may be identical or different, each represents hydrogen, halogen, or alkyl, hydroxy, alkoxy, carboxy, polyhalogenoalkyl, cyano, nitro, alkoxycarbonyl, cycloalkyloxycarbonyl, amino, carbamoyl, sulfo, alkylsulfonyl, cycloalkylsulfonyl or aminosulfonyl, their isomers, and addition salts thereof with a pharmaceutically-acceptable acid or base, and medicinal products containing the same which are useful as PDE IV inhibitors.

12 Claims, No Drawings

SUBSTITUTED BIPHENYL COMPOUNDS

The present invention relates to new substituted biphenyl or phenylpyridine compounds.

BACKGROUND OF THE INVENTION

Those compounds are inhibitors of group IV phosphodiesterases and, for that reason, have especially valuable therapeutic applications.

The functions of most organic tissues are modulated by endogenous substances (hormones, neurotransmitters, autacoids) or by exogenous substances. For some of those substances, the biological effect is relayed at intracellular level by enzyme effectors, such as adenylate cyclase or guanylate cyclase. Stimulation of the enzymes that are responsible for the synthesis of cyclic nucleotides, such as cyclic adenosine-3',5'-monophosphate (cAMP) and cyclic guanosine-3',5'-monophosphate (cGMP), causes an increase in the intracellular level of those second messengers involved in regulating numerous biological functions (E. W. SUTHERLAND and W. RALL, Pharmacol. Rev., Vol. 12, p. 265, 1960). Breakdown of the cyclic nucleotides is effected by a family of enzymes, called phosphodiesterases (PDE), currently classified in 7 groups. The recognition of different isoforms within each of those groups, and of the tissue-specific or cell-specific distribution of certain isoforms, has stimulated research into increasingly specific inhibitors of individual types of isoenzyme (J. A. BEAVO, Physiological Rev., Vol. 75, no. 4, pp. 725–749, 1995). Of the various PDE families, PDE IV has been identified in a large number of tissues or cells, such as brain, heart, vascular endothelium, vascular and tracheobronchial smooth muscle and haematopoietic cells. Inhibition of the phosphodiesterases slows down the hydrolysis of the cyclic nucleotides and brings about an increase in cAMP and/or cGMP level.

PDE IV inhibitors, which are responsible for an increase in cAMP levels, have anti-inflammatory activities and relaxant effects on tracheobronchial smooth muscle, hence their therapeutic value in the field of respiratory pathology and pathologies associated with an inflammatory process (M. N. PALFREYMAN, Drugs of the Future, Vol. 20, no. 8, pp. 793–804, 1995; J. P. BARNES, Eur. Respir. J., Vol. 8, pp. 457–462, 1995; S. B. CHRISTENSEN and T. J. TORPHY, Annual Reports in Medicinal Chemistry, Vol. 29, pp. 185–194, 1994, Academic Press).

Those compounds which are inhibitors of group IV phosphodiesterases will be especially valuable in therapeutic applications concerned with inflammation and bronchial relaxation and more precisely in asthma and chronic obstructive bronchopathies (A. J. DUPLANTIER and J. B. CHENG, Annu. Rep. Med. Chem., Vol. 29, p. 73–81, 1994), (C. D. NICHOLSON and M. SHAHID, Pulmonary Pharmacol., Vol. 7, p. 1–17, 1994), (T. J. TORPHY, G. P. LIVI and S. B. CHRISTENSEN, Drug News Perspect., Vol. 6, p. 03–214, 1993), (J. A. LOWE and J. B. CHENG, Drugs Future, Vol. 17, p. 799–807, 1992), but also in all disorders such as rhinites (I. RADERER, E. HAEN, C. SCHUDT and B. PRZYBILLA, Vienna. Med. Wochenschr., Vol. 145, p. 456–8, 1995), acute respiratory distress syndrome (ARDS) (C. R. TURNER, K. M. ESSER and E. B. WHEELDON, Circulatory Shock, Vol. 39, p. 237–45, 1993), allergies and dermatites (J. M. HANIFIN and S. C. CHAN, J. Invest. Dermatol., Vol. 105, p. 84S–88S, 1995), (J. M. HANIFIN, J. Dermatol. Sci., Vol. 1, p. 1–6, 1990), psoriasis (E. TOUITOU, N. SHACO-EZRA, N. DAYAN, M. JUSHYNSKI, R. RAFAELOFF and R. AZOURY, J. Pharm. Sci., Vol. 81, p. 131–4, 1992), (F. LEVI-SCHAFFER and E. TOUITOU, Skin Pharmacol., Vol. 4, p. 286–90, 1991), rheumatoid arthritis (J. M. ANAYA and L. R. ESPINOZA, J. Rheumatol., Vol. 22, p. 595–9, 1995), autoimmune diseases, (C. P. GENAIN et al. Proc. Natl. Acad. Sci., Vol. 92, p. 3601–5, 1995), multiple sclerosis (N. SOMMER et al., Nat. Med., Vol. 1, p. 244–8, 1995), dyskinesias (T. KITATANI, S. HAYASHI and T. SAKAGUCHI, Nippon. Yakurigaku. Zasshi, Vol. 86, p. 353–8, 1985), glomerulonephritis (M. HECHT, M. MULLER, M. L. LOHMANN-MATTHES and A. EMMENDORFFER, J. Leukoc. Biol., Vol. 57, p. 242–249, 1995), osteoarthritis and septic shock (A. M. BADGER, D. L. OLIVERA and K. M. ESSER Circ. Shock, Vol. 44, p. 188–195, 1994; L. SEKUT et al., Clin. Exp. Inmunol., Vol. 100, p. 126–132, 1995), AIDS (T. F. GRETEN, S. ENDRES et al., AIDS, Vol. 9, p. 1137–1144, 1995), depression (N. A. SACCOMANO et al., J. Med. Chem., Vol. 34, p.291–298, 1991), and any neurodegenerative disease that is accompanied by inflammatory symptoms, such as Alzheimer's disease, Parkinson's disease, Huntington's disease, Down's syndrome and amyotrophic lateral sclerosis (G. Z. FEUERSTEIN et al., Ann. N. Y. Acad. Sci., Vol. 765, p. 62–71, 1995).

Those therapeutic indications are not limiting inasmuch as a decrease in cellular cAMP concentration, whatever the cause and tissue location, results in cellular malfunction, giving rise to pathological symptoms, and may constitute an important therapeutic target for the products described.

DESCRIPTION OF THE PRIOR ART

The closest prior art to the present invention is illustrated especially by the compounds described in the patent specification WO 96/03396, which describes dihydrobenzofuran compounds as anti-inflammatory agents.

DETAILED DESCRIPTION OF THE INVENTION

The present invention relates more especially to compounds of formula (I):

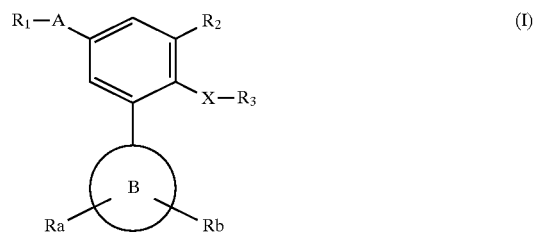

wherein:

$R_1$ represents a substituted or unsubstituted ($C_3$–$C_7$)-cycloalkyl group, a substituted or unsubstituted phenyl group, a substituted or unsubstituted naphthyl group, a saturated or unsaturated, substituted or unsubstituted, mono- or bi-cyclic heterocyclic group containing from 1 to 3 hetero atoms selected from nitrogen, oxygen and sulphur, a linear or branched, substituted or unsubstituted ($C_1$–$C_6$)-alkyl group or a linear or branched, substituted or unsubstituted ($C_1$–$C_6$)-alkenyl group;

A represents a bond (with the proviso that in that case $R_1$ is other than a $C_1$- or $C_2$-alkyl group), an oxygen atom, a sulphur atom, a group

a group

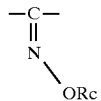

or a group

(wherein Rc represents a hydrogen atom, a linear or branched $(C_1-C_6)$-alkyl group or a $(C_3-C_7)$-cycloalkyl group), $R_2$ represents a halogen atom, a linear or branched, substituted or unsubstituted $(C_1-C_6)$-alkyl group, a linear or branched $(C_1-C_6)$ alkylcarbonyl group, a linear or branched, substituted or unsubstituted $(C_1-C_6)$-alkenyl group, a linear or branched, substituted or unsubstituted $(C_1-C_6)$-alkynyl group, a substituted or unsubstituted $(C_3-C_7)$-cycloalkyl group, a $(C_3-C_7)$-cycloalkylcarbonyl group, a formyl group, a carboxy group, a linear or branched $(C_1-C_6)$-alkoxycarbonyl group, a $(C_3-C_7)$-cycloalkyloxycarbonyl group, a carbamoyl group (optionally substituted by one or two groups selected from linear or branched $(C_1-C_6)$-alkyl, $(C_3-C_7)$-cycloalkyl, hydroxy, linear or branched $(C_1-C_6)$-alkoxy and $(C_3-C_7)$-cycloalkoxy, or forming together with the nitrogen atom carrying them a 5 to 7 chain members ring containing from 1 to 3 heteroatoms selected from nitrogen, oxygen or sulfur), an amino group (optionally substituted by one or two groups selected from linear or branched $(C_1-C_6)$-alkyl, linear or branched $(C_1-C_6)$-acyl and $(C_3-C_7)$-cycloalkyl, or forming together with the nitrogen atom carrying them a 5 to 7 chain members ring containing from 1 to 3 heteroatoms selected from nitrogen, oxygen or sulfur), a formylamino group, a cyano group, an amidino group (optionally substituted by one or two groups selected from linear or branched $(C_1-C_6)$-alkyl and $(C_3-C_7)$-cycloalkyl, or forming together with the nitrogen atom carrying them a 5 to 7 chain members ring containing from 1 to 3 heteroatoms selected from nitrogen, oxygen or sulfur), a hydroxy-aminomethyl group (optionally substituted, independently on the nitrogen or oxygen atom, by a linear or branched $(C_1-C_6)$-alkyl group, a $(C_3-C_7)$-cycloalkyl group or a linear or branched $(C_1-C_6)$-acyl group), an amide oxime group (optionally substituted, independently on the nitrogen or oxygen atom, by a linear or branched $(C_1-C_6)$-alkyl group or a $(C_3-C_7)$-cycloalkyl group, or forming together with the nitrogen atom carrying them a 5 to 7 chain members ring containing from 1 to 3 heteroatoms selected from nitrogen, oxygen or sulfur), a hydrazono group (optionally substituted by one or two groups selected from linear or branched $(C_1-C_6)$-alkyl and $(C_3-C_7)$-cycloalkyl, or forming together with the nitrogen atom carrying them a 5 to 7 chain members ring containing from 1 to 3 heteroatoms selected from nitrogen, oxygen or sulfur), or a group selected from:

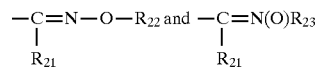

wherein:

$R_{21}$ represents a hydrogen atom, a linear or branched $(C_1-C_6)$-alkyl group or a $(C_3-C_7)$-cycloalkyl group, $R_{22}$ represents a hydrogen atom, a linear or branched $(C_1-C_6)$-alkyl group, a $(C_3-C_7)$-cycloalkyl group or a linear or branched $(C_1-C_6)$-acyl group, $R_{23}$ represents a linear or branched $(C_1-C_6)$-alkyl group or a $(C_3-C_7)$-cycloalkyl group, $R_3$ represents a hydrogen atom, a linear or branched $(C_1-C_6)$-alkyl group, a $(C_3-C_7)$-cycloalkyl group or a linear or branched $(C_1-C_6)$-acyl group, or

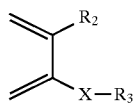

together form the ring

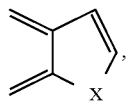

X represents an oxygen atom, a sulphur atom or an NR" group (in which R" represents a hydrogen atom, a linear or branched $(C_1-C_6)$-alkyl group, a $(C_3-C_7)$-cycloalkyl group or a linear or branched $(C_1-C_6)$-acyl group), the ring B is a phenyl or pyridyl ring, Ra and Rb, which may be identical or different, each represents a hydrogen atom, a halogen atom, a linear or branched $(C_1-C_6)$-alkyl group, a hydroxy group, a linear or branched $(C_1-C_6)$-alkoxy group, a carboxy group, a linear or branched $(C_1-C_6)$-polyhalogenoalkyl group, a cyano group, a nitro group, a linear or branched $(C_1-C_6)$-alkoxycarbonyl group, a $(C_3-C_7)$-cycloalkyloxycarbonyl group, an amino group (optionally substituted by one or two linear or branched $(C_1-C_6)$-alkyl, linear or branched $(C_1-C_6)$-acyl or $(C_3-C_7)$-cycloalkyl groups), a carbamoyl group (optionally substituted by one or two linear or branched $(C_1-C_6)$-alkyl, $(C_3-C_7)$-cycloalkyl or linear or branched $(C_1-C_6)$-alkoxy groups), a sulfo group, a linear or branched $(C_1-C_6)$-alkylsulfonyl group, or a aminosulfonyl group (optionally substituted by one on two linear or branched $(C_1-C_6)$-alkyl group or $(C_3-C_7)$-cycloalkyl group), with the proviso that when A represents a bond or an oxygen atom, B represents a phenyl ring, $R_1$ represents a substituted or unsubstituted $(C_3-C_7)$-cycloalkyl group, a substituted or unsubstituted phenyl group or a substituted or unsubstituted naphthyl group, X represents an oxygen atom or an NR" group (in which R" represents a hydrogen atom or a linear or branched $(C_1-C_6)$-alkyl group) and $R_3$ represents a hydrogen atom or a linear or branched $(C_1-C_6)$-alkyl group, then $R_2$ is other than a carboxy group, their isomers and the addition salts thereof with a pharmaceutically-acceptable acid or base.

Among the pharmaceutically acceptable acids there may be mentioned by way of non-limiting example hydrochloric, hydrobromic, sulphuric, phosphonic, acetic, trifluoroacetic, lactic, pyruvic, malonic, succinic, glutaric, fumaric, tartaric, maleic, citric, ascorbic, oxalic, methanesulphonic, camphoric acid, etc . . .

Among the pharmaceutically acceptable bases there may be mentioned by way of non-limiting example sodium hydroxide, potassium hydroxide, triethylamine, tert-butylamine, etc . . . Among the preferred compounds of the present invention there may be mentioned compounds in which X represents an oxygen atom, those in which B represents a phenyl ring, and those in which $R_1$ represents a substituted or unsubstituted phenyl ring, or a substituted or unsubstituted pyridyl.

Among the saturated or unsaturated, mono- or bicyclic heterocyclic groups containing from 1 to 3 hetero atoms selected from nitrogen, oxygen and sulphur there may be mentioned as preferred the groups furyl, thienyl, pyridyl and imidazolyl.

There is to be understood by substituted alkyl, substituted alkenyl, substituted alkynyl or substituted cycloalkyl, substitution by one or more halogen atoms or by one or more of the groups linear or branched $(C_1-C_6)$-alkoxy, linear or branched $(C_1-C_6)$-alkylthio, $(C_3-C_7)$-cycloalkyl, substituted or unsubstituted phenyl, substituted or unsubstituted naphthyl or substituted or unsubstituted heterocyclyl (such as, for example, a pyridyl group). A preferred saturated or unsaturated substituted alkyl group is the substituted or unsubstituted benzyl group.

There is to be understood by substituted phenyl, substituted naphthyl, substituted heterocyclyl or substituted benzyl, substitution by one or more halogen atoms or linear or branched $(C_1-C_6)$-alkyl, linear or branched $(C_1-C_6)$-alkoxy or trihalogenomethyl groups.

The present invention extends also to a process for the preparation of compounds of formula (I) which is characterised in that there is used as starting material a compound of formula (II):

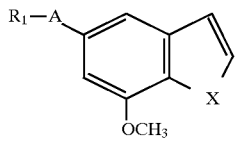

wherein $R_1$, A and X are as defined for formula (I), which is subjected to the action of boron tribromide in dichloromethane medium to yield a compound of formula (III):

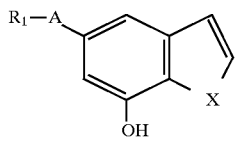

wherein $R_1$, A and X are as defined for formula (I), which is subjected to the action of trifluoromethanesulphonic anhydride in pyridine to yield a compound of formula (IV):

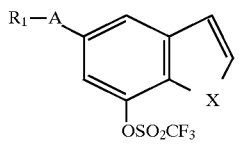

wherein $R_1$, A and X are as defined for formula (I), which is subjected to the action of a boric acid of formula (V):

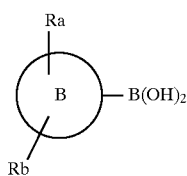

wherein B, Ra and Rb are as defined for formula (I), to yield a compound of formula (I/a):

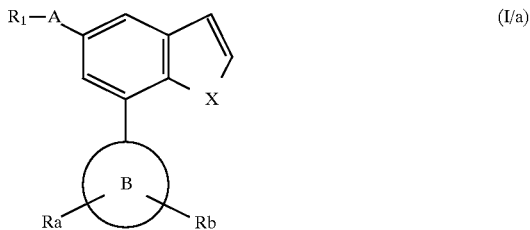

wherein $R_1$, A, Ra, Rb, B et X are as defined for formula (I), a particular case of compounds of formula (I), which compound of formula (I/a) is, if desired, subjected to oxidative cleavage to yield a compound of formula (I/b):

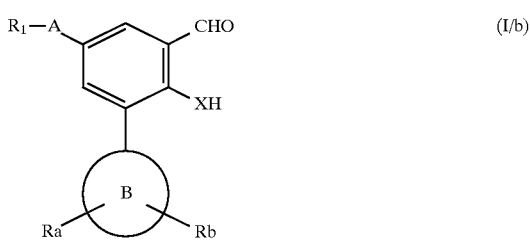

wherein $R_1$, A, Ra, Rb, B and X are as defined for formula (I), a particular case of compounds of formula (I), which compound of formula (I/b) may be subjected:

a to the action of a compound of formula (VI):

wherein $R_{22}$ represents a hydrogen atom, a linear or branched $(C_1-C_6)$-alkyl group, a $(C_3-C_7)$-cycloalkyl group or a linear or branched $(C_1-C_6)$-acyl group, in basic medium, to yield a compound of formula (I/c):

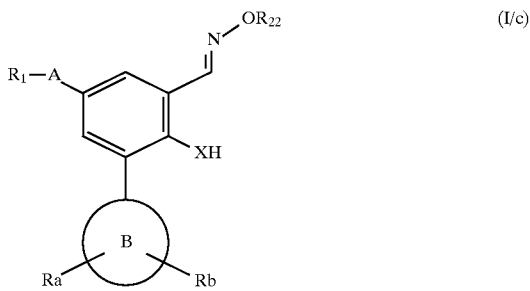

wherein $R_1$, A, Ra, Rb, B, X and $R_{22}$ are as defined hereinbefore, a particular case of compounds of formula (I),
which compound of formula (I/c) is optionally converted in acid medium when $R_{22}$ is different from an acyl group to a compound of formula (I/d):

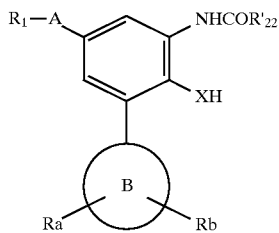
(I/d)

wherein $R_1$, A, Ra, Rb, B, X and Rc are as defined hereinbefore and $R'_{22}$, different from an acyl group, has the same definition than $R_{22}$, a particular case of compounds of formula (I), b or to the action, in alcoholic medium, of a hydroxylamine of formula $R_{23}NH$—OH wherein $R_{23}$ represents a linear or branched $(C_1-C_6)$-alkyl group or a $(C_3-C_7)$-cycloalkyl group to yield a compound of formula (I/e):

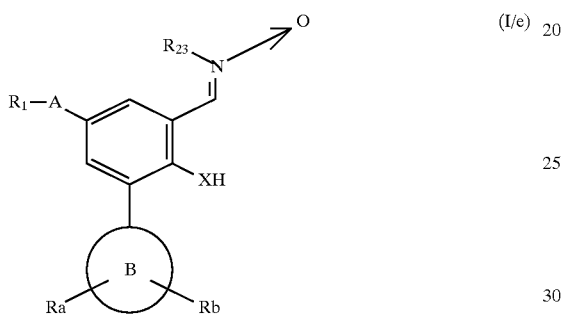
(I/e)

wherein $R_1$, A, B, Ra, Rb, X and $R_{23}$ are as defined hereinbefore, a particular case of compounds of formula (I), c or to the action of a phosphorus yield of formula $R'cCH_2P^+(C_6H_5)_3Br^-$ (wherein R'c represents a hydrogen atom, a linear or branched $(C_1-C_6)$-alkyl group, a $(C_3-C_7)$-cycloalkyl group, a linear or branched $(C_1-C_6)$-alkoxy group, a linear or branched $(C_1-C_6)$-alkylthio group, a substituted or unsubstituted phenyl group, a substituted or unsubstituted naphthyl group or a saturated or unsaturated, substituted or unsubstituted heterocyclic group) in the presence of n-butyllithium, to yield a compound of formula (I/f):

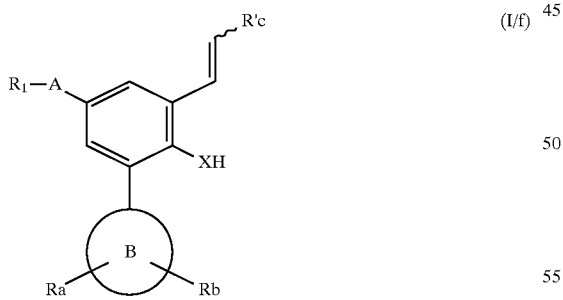
(I/f)

wherein $R_1$, A, Ra, Rb, B, X and R'c are as defined hereinbefore, a particular case of compounds of formula (I),
which, if desired, is subjected to reduction to yield a compound of formula (I/g):

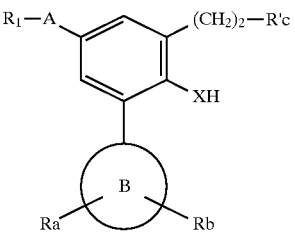
(I/g)

wherein $R_1$, A, Ra, Rb, B, X et R'c are as defined hereinbefore, a particular case of compounds of formula (I), d or to a reaction in oxidising medium to yield a compound of formula (I/h):

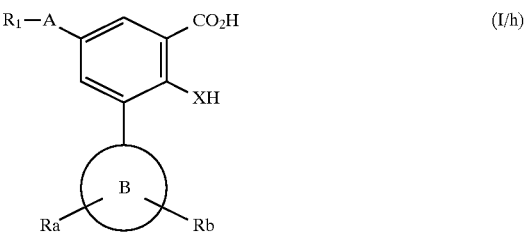
(I/h)

wherein $R_1$, A, Ra, Rb, B and X are as defined for formula (I), the acid function of which compound of formula (I/h) is converted into the corresponding acid chloride, which may then be converted into the corresponding ester, amide or amine according to conventional reactions in organic chemistry, e or to the action of hydroxylamine hydrochloride in an appropriate medium to yield a compound of formula (I/i):

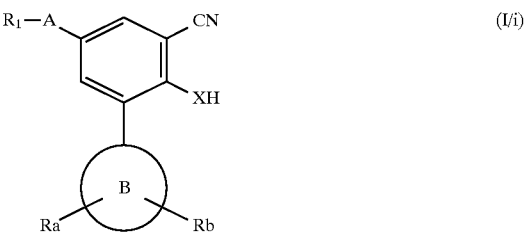
(I/i)

wherein $R_1$, A, Ra, Rb, B and X are as defined hereinbefore, a particular case of compounds of formula (I),
which is reacted in alcoholic medium with hydrochloric acid, and then with an amine Rd—NH—Re (wherein Rd and Re, which may be identical or different, each represents a hydrogen atom, a linear or branched $(C_1-C_6)$-alkyl group or a cycloalkyl group, or form together with the nitrogen atom carrying them a ring having from 5 to 7 chain members), to yield a compound of formula (I/j):

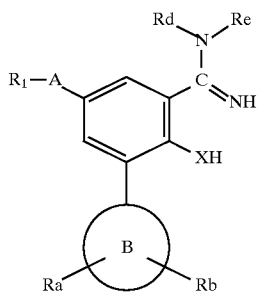

wherein $R_1$, A, Ra, Rb, X, B, Rd and Re are as defined hereinbefore, a particular case of compounds of formula (I), or is reacted in basic medium with a compound of formula (VI):

wherein Rc is as defined hereinbefore,
to yield a compound of formula (I/k):

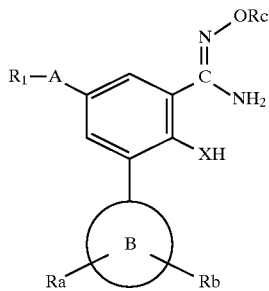

wherein A, B, $R_1$, Ra, Rb, Rc and X are as defined hereinbefore, a particular case of compounds of formula (I), f or, finally, with a hydrazine

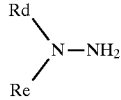

(Rd and Re being as defined hereinbefore)
to yield a compound of formula (I/l):

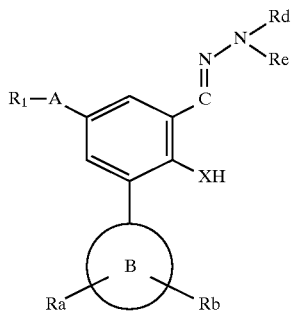

wherein A, B, $R_1$, Ra, Rb, Rd, Re and X are as defined hereinbefore, a particular case of compounds of formula (I),
which compound of formula (I/a), (I/b), (I/c), (I/d), (I/e), (I/f), (I/g), (I/h), (I/i), (I/l) or a derivative thereof:
is, if desired, subjected to the action of a dialkyl sulphate or a linear or branched $(C_1-C_6)$-alkyl halide or a linear or branched $(C_1-C_6)$-acyl halide or a $(C_3-C_7)$-cycloalkyl halide,
to yield a compound of formula (I/m):

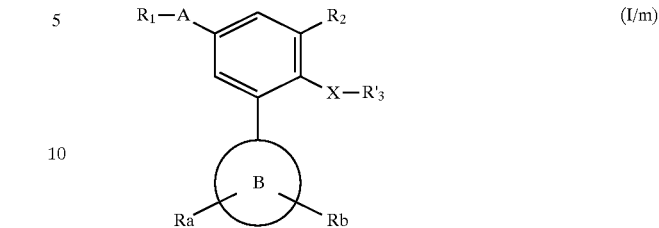

wherein $R_1$, A, B, Ra, Rb, $R_2$ and X are as defined hereinbefore and $R'_3$ represents a linear or branched $(C_1-C_6)$-alkyl group, a linear or branched $(C_1-C_6)$-acyl group or a $(C_3-C_7)$-cycloalkyl group, a particular case of compounds of formula (I),
which compound of formula (I/a) to (I/m) or a derivative thereof:
  may, if necessary, be purified according to a conventional purification technique,
  is, where appropriate, separated into its isomers according to a conventional separation technique,
  is, if desired, converted into its addition salts with a pharmaceutically acceptable acid or base.

The compounds of formula (II) are generally prepared from an aldehyde of formula (VII):

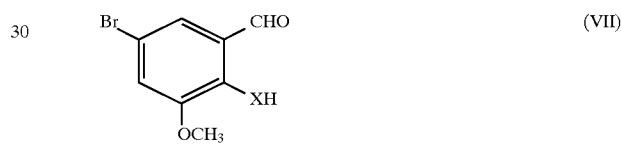

wherein X is as defined for formula (I),
which is reacted with 2-bromo-1,1-dimethoxyethane in an appropriate medium to yield a compound of formula (VIII):

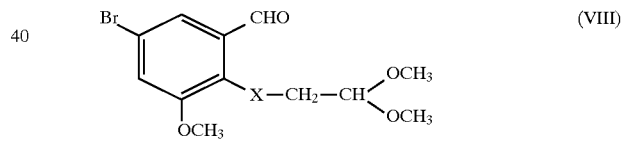

wherein X is as defined for formula (I),
which is cyclised in acid medium to yield a compound of formula (IX):

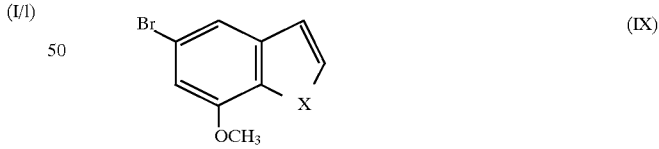

wherein X is as defined for formula (I),
which compound of formula (IX) is subjected:
  to the action of an organo-zinc compound of formula $R_1$—$CH_2$—ZnBr (wherein $R_1$ is as defined for formula (I)),
  or, after previous reaction with hexabutylditin, to the action of an acid chloride of formula $R_1$—CO—Cl (wherein $R_1$ is as defined for formula (I)), in the presence of palladium catalyst, it being understood that the carbonyl function may optionally be reduced to the hydroxide by reducing agents conventionally employed in organic chemistry provided that is compatible with the substituents present on the molecule, or, after previous reaction of an ethylenic compound of the formula

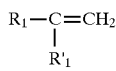

(wherein $R_1$ is as defined for formula (I) and $R'_1$ represents a hydrogen atom, a linear or branched $(C_1-C_6)$-alkyl group, or a $(C_3-C_7)$-cycloalkyl group) with 9-borabicyclo[3.3.1]nonane, then reaction in the presence of a palladium catalyst, or, in the presence of a palladium catalyst, to the action of a compound of formula (X):

 (X)

wherein $R_1$ is as defined for formula (I) and Y represents a sulphur or oxygen atom, to yield a compound of formula (II).

Certain compounds of formula (I) may advantageously be obtained using as starting material, when it is available, a compound of formula (XI):

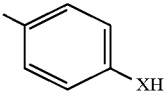 (XI)

wherein X, A and $R_1$ are as defined for formula (I), which is subjected to a bromination reaction to yield a compound of formula (XII)

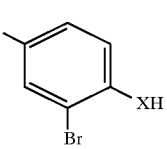 (XII)

wherein X, A and $R_1$ are as defined hereinbefore, which is subjected to the action of a boric acid of formula (V):

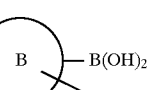 (V)

wherein Ra, Rb and B are as defined for formula (I), to yield a compound of formula (XIII):

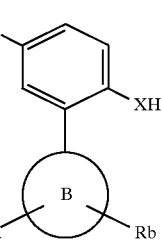 (XIII)

wherein A, $R_1$, Ra, Rb, B and X are as defined hereinbefore, which compound (XIII) is subjected to a halogenation reaction to yield a compound of formula (I/n):

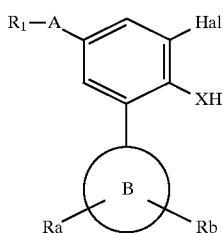 (I/n)

wherein A, $R_1$, Ra, Rb, B and X are as defined hereinbefore and Hal represents a halogen atom, a particular case of compounds of formula (I), which compound (I/n) may be subjected:

either to the action of zinc cyanide in the presence of a palladium catalyst to yield a compound of formula (I/i) as defined hereinbefore, or to the action of 1-ethoxyvinyltributyltin in the presence of a palladium catalyst to yield a compound of formula (I/p):

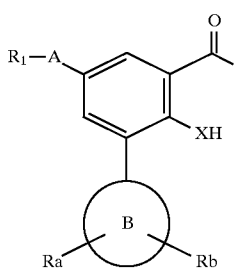 (I/p)

wherein A, $R_1$, Ra, Rb, B and X are as defined for formula (I), and $R_{21}$, different from a hydrogen atom, has the same definition as in formula (I), a particular case of compounds of formula (I), which compound (I/p) is reacted:

either with a compound of formula (VI):

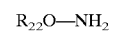 (VI)

wherein $R_{22}$ is as defined hereinbefore, to yield a compound of formula (I/q):

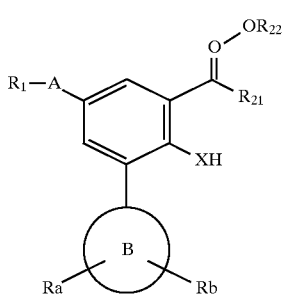 (I/q)

wherein A, B, $R_1$, Ra, Rb, $R_{21}$, $R_{22}$ and X are as defined hereinbefore, a particular case of compounds of formula (I);

or with a hydrazine

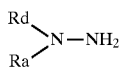

(Rd and Re being as defined hereinbefore)

to yield a compound of formula (I/s):

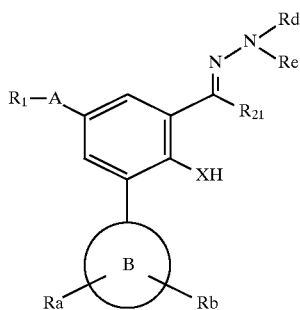

wherein A, B, $R_1$, Ra, Rb, $R_{21}$ and X are as defined hereinbefore, a particular case of compounds of formula (I), which compound (I/n), (I/p), (I/q), (I/s) or a derivative thereof is optionally subjected to the action of an dialkylsulfate or a linear or branched ($C_1$–$C_6$)-alkyl halide, a linear or branched ($C_1$–$C_6$)-acyl halide or a ($C_3$–$C_7$)-cycloalkyl halide to yield a compound of formula (I/m) as defined hereinbefore, which compound (I/n) to (I/s) or a derivative thereof:
- may, if necessary, be purified according to a conventional purification technique,
- is, where appropriate, separated into its isomers according to a conventional separation technique,
- is, if desired, converted into its addition salts with a pharmaceutically acceptable acid or base.

The present invention relates also to pharmaceutical compositions comprising as active ingredient at least one compound of formula (I), alone or in combination with one or more inert, non-toxic excipients or carriers.

Among the pharmaceutical compositions according to the invention there may be mentioned more especially those which are suitable for oral, parenteral or nasal administration, tablets or dragées, sublingual tablets, gelatin capsules, lozenges, suppositories, creams, ointments. dermal gels, aerosols, etc.

The dosage used varies according to the age and weight of the patient, the nature and severity of the disorder and also the administration route, which may be oral, nasal, rectal or parenteral. Generally, the unit dosage ranges from 10 to 5000 mg for a treatment of from 1 to 3 doses per 24 hours.

The following Examples illustrate the invention and do not limit it in any way.

The starting materials used are known products or are products prepared according to known methods of operation.

The structures of the compounds described in the Examples were determined according to customary spectrophotometric techniques (infrared, NMR, mass spectrometry . . . ).

EXAMPLE 1

5-Benzyl-7-(3-nitrophenyl)benzo[b]furan

Step A: 5-Bromo-2-(2,2-dimethoxyethoxy)-3-methoxybenzaldehyde

A heterogeneous solution of 31 g (0.134 mol) of 5-bromo-2-hydroxy-3-methoxybenzaldehyde, 28 g (0.166 mol) of 2-bromo-1,1-dimethoxyethane and 49 g (0.150 mol) of caesium carbonate in 150 ml of dimethylformamide is heated at 160° C. for 3 hours. After returning to room temperature, the mixture is filtered. The filtrate is then evaporated under reduced pressure. The solid so obtained is taken up in 250 ml of dichloromethane and filtered again. The homogeneous solution is then washed twice with 200 ml of 0.1N hydrochloric acid each time and subsequently with 200 ml of a saturated sodium chloride solution. The organic phase is then dried over sodium sulphate and subsequently evaporated under reduced pressure, yielding the expected product.

Step B: 5-Bromo-7-methoxybenzo[b]furan

The product obtained in the preceding Step is dissolved in 1000 ml of 20% sulphuric acid and heated at reflux for 3 hours. After cooling to room temperature, the solution is neutralised with potassium carbonate and then extracted twice with 300 ml of ethyl acetate each time. The organic phases are subsequently combined, dried over sodium sulphate, filtered, and then concentrated under reduced pressure.

The residue is purified by chromatography on a silica column using a dichloromethane/heptane (1/1) mixture as eluant, yielding the expected product in the form of a colourless oil which crystallises in the cold.

Step C: 5-Benzyl-7-methoxybenzo[b]furan 12.3 g (0.188 g.atm) of powdered zinc are covered with 15 ml of tetrahydrofuran to which a few drops of dibromoethane are added, and the whole is placed under an argon atmosphere. The solution is heated rapidly and a few drops of a solution of 29.4 g (0.171 mol) of benzyl bromide in 135 ml of tetrahydrofuran are added. When the reaction has been initiated, the reaction mixture is cooled to +4° C., and the addition of the remaining benzyl bromide solution is carried out at that temperature (addition time approximately 1 hour). The mixture is then stirred at +4° C. for 2 to 3 hours. The solution is subsequently added dropwise to a mixture of 19.5 g (0.086 mol) of the compound obtained in the preceding step and 5.18 g ($4.47 \times 10^{-3}$ mol) of tetrakis (triphenylphosphine)palladium(0) in 150 ml of tetrahydrofuran under an argon atmosphere. The reaction mixture is heated at reflux for 15 hours. After returning to room temperature, the reaction mixture is diluted with 300 ml of ethyl acetate and then washed in succession with 200 ml of water and 200 ml of a saturated sodium chloride solution. Customary treatment of the organic phase yields an oil, which is purified by chromatography on a silica column using a dichloromethane/heptane (1/1) mixture as eluant and yields the expected product in the form of an oil.

Step D: 5-Benzyl-7-hydroxybenzo[b]furan

A solution of 18 g (0.0755 mol) of the compound obtained in the preceding Step and 150 ml of dichloromethane is added, under an argon atmosphere, to a solution of 155 ml of 1M boron tribromide in dichloromethane at −78° C. The reaction mixture gradually increased to a temperature of −5° C. (about 15 hours). At that temperature, 150 ml of water are poured in and the organic phase is separated off. The aqueous phase is saturated with sodium chloride and re-extracted using 100 ml of dichloromethane. The organic phases are then combined, dried over sodium sulphate, filtered and concentrated under reduced pressure. The residue is purified by chromatography on a silica column using dichloromethane as eluant, and yields the expected product in the form of an oil.

Step E: 5-Benzyl-7-trifluoromethanesulphonyloxybenzo[b]furan

Under an inert atmosphere and at 0° C., 18.3 g (0.0649 mol) of trifluoromethanesulphonic anhydride are poured dropwise into a solution of 9.1 g (0.04057 mol) of the compound obtained in the preceding Step in 60 ml of pyridine. After 2 hours, the solution is concentrated under reduced pressure. The residue is taken up using 100 ml of dichloromethane and washed in succession with 150 ml of a 2N hydrochloric acid solution, 150 ml of a saturated sodium hydrogen carbonate solution and finally 150 ml of a saturated sodium chloride solution. Customary treatment of the organic phase yields the expected product in semi-solid form.

Step F: 5-Benzyl-7-(3-nitrophenyl)benzo[b]furan

Under an inert atmosphere, a mixture of 11.1 g (0.08 mol) of potassium carbonate, 13 g 0.0364 mol) of the compound described in the preceding Step, 8.6 g (0.05 mol) of 3-nitrophenylboric acid and 1.49 g ($1.82 \times 10^{-3}$ mol) of bis(diphenylphosphino)ferrocene palladium(II) chloride in 250 ml of dimethylformamide is heated at 80° C. for 18 hours. After concentration of the solvent under reduced pressure, the residue is taken up in 200 ml of ethyl acetate and washed with 200 ml of water and then 200 ml of a saturated sodium chloride solution. Customary treatment of the organic phase followed by purification by chromatography on a silica column (eluant:toluene/heptane 6/4 then 8/1) allows 10.11 g (0.0307 mol) of a pale yellow oil to be obtained.

Elemental microanalysis:

|  | C% | H% | N% |
| --- | --- | --- | --- |
| calculated | 77.07 | 4.82 | 4.13 |
| found | 76.58 | 4.59 | 4.25 |

EXAMPLE 2

5-(4-Fluorobenzyl)-7-(3-nitrophenyl)benzo[b]furan

Steps A and B are identical to Steps A and B of Example 1.

Step C: 5-(4-Fluorobenzyl)-7-methoxybenzo[b]furan

The expected product is obtained in accordance with the process described in Example 1 by replacing the benzyl bromide in Step C with 4-fluorobenzyl bromide.

Melting point: 76°–78° C.

Steps D, E and F are identical to Steps D, E and F of Example 1.

Step D: 5-(4-Fluorobenzyl)-7-hydroxybenzo[b]furan

Step E: 5-(4-Fluorobenzyl)-7-trifluoromethanesulphonyloxybenzo[b]furan

Step F: 5-(4-Fluorobenzyl)-7-(3-nitrophenyl)benzo[b]furan

Elemental microanalysis:

|  | C% | H% | N% |
| --- | --- | --- | --- |
| calculated | 72.62 | 4.06 | 4.03 |
| found | 72.47 | 4.14 | 4.11 |

EXAMPLE 3

5-(2,6-Dichloro-4-pyridylmethyl)-7-(3-nitrophenyl)benzo[b]furan

The expected product is obtained in accordance with the process described in Example 1 by replacing the benzyl bromide in Step C with 2,6-dichloro-4-pyridylmethyl bromide.

EXAMPLE 4

5-(2-Furoyl)-7-(3-nitrophenyl)benzo[b]furan

Step A: 5-Tributylstannyl-7-methoxybenzo[b]furan

A solution of 10 g (0.044 mol) of 5-bromo-7-methoxybenzo[b]furan described in Step B of Example 1, 51.10 g (0.088 mol) of hexabutylditin and 2.55 g (0.0022 mol) of tetrakis(triphenylphosphine)palladium(0) in 200 ml of toluene is heated at 100° C. for 4 hours under an argon atmosphere. After returning to room temperature, the solution is stirred overnight with a solution of 80 ml of methanolic potassium fluoride. The heterogeneous mixture is then filtered over Celite. The methanol is subsequently evaporated off and the toluene solution remaining is washed with 100 ml of water and then 100 ml of a saturated sodium chloride solution. Customary treatment of the organic phase yields an oil, which is purified by chromatography on a silica column using a toluenelheptane (4/6) mixture as eluant and yields the expected product in the form of an oil.

Step B: 5-(2-Furoyl)-7-methoxybenzo[b]furan

A solution of 5 g (0.0114 mol) of the tin compound described in the preceding Step, 1.49 g (0.0114 mol) of 2-furoyl chloride and 0.12 g (0.000134 mol) of tris(dibenzylidene-acetone)dipalladium(0) in 50 ml of toluene is heated at 75°–80° C. for 1 hour 30 minutes. After returning to room temperature, the solution is filtered over Celite and then washed with 50 ml of water followed by 50 ml of a saturated sodium chloride solution. Customary treatment of the organic phase yields an oil, which is purified by chromatography on a silica column using dichloromethane as eluant.

Melting point: 121°–123° C.

Step C: 5-(2-Furoyl)-7-hydroxybenzo[b]furan

The expected product is obtained in accordance with the process described in Step D of Example 1 starting from the compound obtained in the above Step.

Melting point: 140°–142° C.

Step D: 5-(2-Furoyi)-7-trifluoromethanesulphonyloxybenzo[b]furan

The product is obtained in accordance with the process described in Step E of Example 1 starting from the compound obtained in the above Step.

Step E: 5-(2-Furoyl)-7-(3-nitrophenyl)benzo[b]furan

The expected product is obtained in accordance with the process described in Step F of Example 1 starting from the compound obtained in the above Step.

Melting point: 148°–150° C.

Elemental microanalysis:

|  | C% | H% | N% |
| --- | --- | --- | --- |
| calculated | 68.47 | 3.33 | 4.20 |
| found | 68.42 | 3.56 | 4.48 |

EXAMPLE 5

7-(3-Nitrophenyl)-5-pentylbenzo[b]furan

Step A: 7-Methoxy-5-pentylbenzo[b]furan

Under an inert atmosphere and at 0° C., a solution of 58.2 ml of 0.5 molar 9-BBN is added dropwise to a solution of 2.04 g (0.029 mol) of pentene in 12 ml of tetrahydrofuran. When the addition is complete, the ice bath is removed and the solution is stirred for 3 hours. The solution is then poured dropwise into a solution of 6 g (0.0264 mol) of 5-bromo-7-mnethoxybenzo[b]furan, 0.65 g (0.000796 mol) of palladium complex described in Step F of Example 1, and 24 ml of 3N sodium hydroxide in 84 ml of tetrahydrofuran. The reaction mixture is heated at 65° C. for 15 hours. After returning to room temperature, the solution is diluted with 150 ml of ethyl acetate and washed with water, then with 150 ml of a 0.1N hydrochloric acid solution and finally with 100 ml of a saturated sodium chloride solution. Customary treatment of the organic phase yields an oil, which is purified by chromatography on a silica column using a toluene/cyclohexane (4/6) mixture as eluant.

Step B: 7-Hydroxy-5-pentylbenzo[b]furan

The expected product is obtained in accordance with the process described in Step D of Example 1 starting from the compound obtained in the above Step.

Step C: 5-Pentyl-7-trifluoromethanesulphonyloxybenzo[b]furan

The product is obtained in accordance with the process described in Step E of Example 1 starting from the compound obtained in the above Step.

Step D: 7-(3-Nitrophenyl)-5-pentylbenzo[b]furan

The expected product is obtained in accordance with the process described in Step F of Example 1 starting from the compound obtained in the above Step.

Elemental microanalysis:

|            | C%    | H%   | N%   |
|------------|-------|------|------|
| calculated | 73.77 | 6.19 | 4.53 |
| found      | 74.43 | 6.28 | 4.65 |

EXAMPLES 6 and 7

EXAMPLE 6

5-Allyl-7-(3-nitrophenyl)benzo[b]furan

EXAMPLE 7

(E)-7-(3-Nitrophenyl)-5-(prop-1-enyl)benzo[b]furan
Step A: 5-Allyl-7-methoxybenzo[b]furan A solution of 10 g (0.044 mol) of 5-bromo-7-methoxybenzo[b]furan, 17.5 g (0.053 mol) of allyltributyltin and 1.02 g (0.00088 mol) of tetrakis(triphenylphosphine)palladium(0) in 80 ml of dimethylformamide is heated at 90° C. for 15 hours under an inert atmosphere. After returning to room temperature, the dimethylformamide is evaporated off in vacuo. The reaction mass is taken up in 200 ml of diethyl ether and washed in succession with 100 ml of water and 100 ml of a saturated sodium chloride solution. Customary treatment of the organic phase yields an oil, which is purified by chromatography on a silica column using a dichloromethane/heptane (6/4) mixture as eluant.

Step B: Mixture of 5-allyl-7-trifluoromethanesulphonyloxybenzo[b]furan ($B_1$) and (R,S)-5-(2-bromoprop-1-yl)-7-trifluoromethanesulphonyloxybenzo[b]furan ($B_2$)

The mixture of these two compounds is obtained by carrying out in succession the processes described in Steps D and E of Example 1 starting from the compound described in the above Step. The compounds $B_1$ and $B_2$ are separated by chromatography on a silica column using a toluene/heptane (2/8) mixture as eluant.

5-Allyl-7-(3-nitrophenyl)benzo[b]furan

The expected product is obtained in accordance with the process described in Step F of Example 1 starting from the compound $B_1$ obtained in the above Step.

Elemental microanalysis:

|            | C%    | H%   | N%   |
|------------|-------|------|------|
| calculated | 72.11 | 4.69 | 5.01 |
| found      | 72.60 | 4.93 | 5.07 |

(E)-7-(3-Nitrophenyl)-5-(prop-1-enyl)benzo[b]furan

The expected product is obtained in accordance with the process described in Step F of Example 1 starting from the compound $B_2$ obtained in the above Step.

Melting point: 103°–105° C.

Elemental mnicroanalysis:

|            | C%    | H%   | N%   |
|------------|-------|------|------|
| calculated | 72.11 | 4.69 | 5.01 |
| found      | 72.31 | 4.95 | 4.99 |

EXAMPLE 8

5-Benzyl-2-hydroxy-3-(3-nitrophenyl)benzaldehyde

Bubbling with ozone is carried out in a solution of 3.4 g (0.01 mol) of the compound described in Example 1 in 150 ml of dichloromethane coloured with <<Sudan Red>> at −78° C. Decolouration (3 hours) signifies that the reaction is complete. 4.65 g (0.075 mol) of dimethyl sulphide are then added and the solution is stirred overnight at room temperature. The solution is then washed with 50 ml of water and subsequently with 50 ml of a saturated sodium chloride solution. Customary treatment of the organic phase followed by purification by chromatography on a silica column using a dichloromethane/heptane (8/2) mixture as eluant yields the expected product in the form of a colourless oil.

Elemental microanalysis:

|            | C%    | H%   | N%   |
|------------|-------|------|------|
| calculated | 72.06 | 4.54 | 4.20 |
| found      | 71.17 | 4.71 | 4.28 |

EXAMPLE 9

5-(4-Fluorobenzyl)-2-hydroxy-3-(3-nitrophenyl) benzaldehyde

The expected product is obtained in accordance with the process described in Example 8 starting from the compound described in Example 2.

EXAMPLE 10

5-(2,6-Dichloro-4-pyridylmethyl)-2-hydroxy-3-(3-nitrophenyl) benzaldehyde

The expected product is obtained in accordance with the process described in Example 8 starting from the compound described in Example 3.

EXAMPLE 11

5-Benzyl-7-(4-pyridyl-4-yl)benzo[b]furan

The expected product is obtained in accordance with the process described in Example 1 by replacing the 3-nitrophenylboric acid in Step F with 4-pyridylboric acid.

EXAMPLE 12

2-Hydroxy-3-(3-nitrophenyl)-5-pentylbenzaldehyde

The expected product is obtained in accordance with the process described in Example 8 starting from the compound described in Example 5.

EXAMPLE 13

5-Benzyl-7-(3-nitrophenyl)indole

The expected product is obtained in accordance with the process described in Example 1 by replacing the 5-bromo-2-hydroxy-3-methoxybenzaldehyde in Step A with 2-amino-5-bromo-3-methoxybenzaldehyde.

Melting point: 155°–157° C.

Elemental microanalysis:

|  | C% | H% | N% |
|---|---|---|---|
| calculated | 76.81 | 4.91 | 8.53 |
| found | 76.97 | 4.86 | 8.38 |

EXAMPLE 14

2-Amino-5-benzyl-3-(3-nitrophenyl)benzaldehyde

The expected product is obtained in accordance with the process described in Example 8 starting from the compound described in Example 13.

EXAMPLE 15

(E)-5-Benzyl-2-hydroxy-3-(3-nitrophenyl)benzaldehyde oxime

A solution of 0.9 g (0.0027 mol) of the compound described in Example 8 and 0.2 g (0.0028 mol) of hydroxylamine hydrochloride in 8 ml of pyridine is heated at reflux for 1 hour 30 minutes. The solvent is evaporated off and the solid is taken up in 30 ml of dichloromethane. The solution is then washed with 10 ml of a 0.5N hydrochloric acid solution and subsequently with 10 ml of a saturated sodium chloride solution. Customary treatment of the organic phase yields the expected product in solid form.

Melting point: 143°–145° C. (petroleum ether).

EXAMPLE 16

(E)-5-(4-Fluorobenzyl)-2-hydroxy-3-(3-nitrophenyl)benzaldehyde oxime

The expected product is obtained in accordance with the process described in Example 15 starting from the compound described in Example 9.

Melting point: 157°–159° C. (toluene)

Elemental microanalysis:

|  | C% | H% | N% |
|---|---|---|---|
| calculated | 65.57 | 4.13 | 7.65 |
| found | 65.35 | 4.43 | 7.63 |

EXAMPLE 17

(E)-2-Hydroxy-3-(3-nitrophenyl)-5-pentylbenzaldehyde oxime

The expected product is obtained in accordance with the process described in Example 15 starting from the compound described in Example 12.

Melting point: 106°–108° C. (ethanol-water)

EXAMPLE 18

3-Benzyl-6-methoxy-5-(3-nitrophenyl)benzaldehyde

A solution of 0.2 g (0.0006 mol) of the compound described in Example 8, 0.26 g (0.0008 mol) of caesium carbonate and 0.113 g (0.0009 mol) of dimethyl sulphate in 5 ml of acetone is heated at reflux for 1 hour. After returning to room temperature, the solution is filtered and evaporated in vacuo. The solid is taken up in 10 ml of ethyl ether and the solution is washed with water. Customary treatment of the organic phase followed by purification by chromatography on a silica column using a dichloromethane/heptane (7/3) mixture as eluant yields the expected product in the form of an oil.

Elemental microanalysis:

|  | C% | H% | N% |
|---|---|---|---|
| calculated | 72.61 | 4.93 | 4.03 |
| found | 73.36 | 5.56 | 3.68 |

EXAMPLE 19

5-Benzyl-2-hydroxy-3-(3-nitrophenyl)benzaldehyde methyloxime

The expected product is obtained in accordance with the process described in Example 15 by replacing the hydroxylamine hydrochloride with O-methylhydroxylamine hydrochloride.

Elemental microanalysis:

|  | C% | H% | N% |
|---|---|---|---|
| calculated | 69.60 | 5.01 | 7.73 |
| found | 70.00 | 5.12 | 7.73 |

EXAMPLE 20

5-Benzyl-2-methoxy-3-(3-nitrophenyl)benzaldehyde methyloxime

The expected product is obtained in accordance with the process described in Example 19 starting from the compound described in Example 18.

Elemental microanalysis:

|  | C% | H% | N% |
|---|---|---|---|
| calculated | 70.20 | 5.36 | 7.44 |
| found | 70.30 | 5.51 | 7.34 |

EXAMPLE 21

5-Benzyl-2-hydroxy-3-(3-nitrophenyl)benzonitrile

A solution of 0.133 ml (0.00145 mol) of phosphorus oxychloride is added dropwise to a solution of 0.5 g (0.00143 mol) of the compound described in Example 15 in 0.3 ml of dimethylacetamide and 0.9 ml of acetonitrile. The internal temperature of the reaction mixture must not under any circumstance exceed 30° C. during the course of the addition. After half an hour's stirring, the solution is neutralised with a saturated sodium hydrogen carbonate solution and extracted with diethyl ether. Customary treatment of the organic phase followed by chromatography on a silica column using a dichloromethane/ethyl acetate (98/2) mixture as eluant yields the expected product in the form of a white solid.

Melting point: 148°–149° C. (petroleum ether)
Elemental microanalysis:

|  | C% | H% | N% |
| --- | --- | --- | --- |
| calculated | 72.72 | 4.27 | 8.48 |
| found | 72.41 | 4.37 | 8.31 |

EXAMPLE 22

5-Benzyl-2-methoxy-3-(3-nitrophenyl)benzonitrile

The expected product is obtained in accordance with the process described in Example 18 starting from the compound obtained in Example 21.

EXAMPLE 23

N-oxide of [5-(4-fluorobenzyl)-2-hydroxy-3-(3-nitrophenyl)-benzylidene]-methylamine hydrochloride 0.024 g (0.000284 mol) of N-methylhydroxylamine hydrochloride is added in one go to a warm solution of 3 ml of ethanol containing 0.1 g (0.000284 mol) of the compound described in Example 9 and a few molecular sieve beads. The solution is then heated at reflux for 5 hours. After removal of the solvent under reduced pressure, the crude reaction mixture is applied to a silica column using a dichloromethane/ethyl acetate (9/1) mixture as eluant and yields the expected product in the form of a base, which is converted into the corresponding hydrochloride.

Melting point: 92°–95° C. (ethyl ether)

EXAMPLE 24

Methyl 5-(4-fluorobenzyl)-3-(3-nitrophenyl)-2-hydroxybenzoate

Step A: 5-(4-Fluorobenzyl)-3-(3-nitrophenyl)-2-hydroxybenzoic acid 0.267 g (0.00222 mol) of sodium hydrogen phosphate and 0.082 g (0.000837 mol) of sulphamic acid dissolved in 2.2 ml of water are added to a solution of 0.2 g (0.00057 mol) of the compound described in Example 9 in 6.5 ml of dioxane. The reaction mixture is cooled to 10° C., then a solution of 0.067 g (0.00074 mol) of sodium chlorite dissolved in 0.3 ml of water is added dropwise over a period of 20 minutes. The solution is maintained at 10° C. for 1 hour and is then slowly reheated to room temperature. After 2 hours, 0.0848 g (0.00067 mol) of sodium sulphite is added in one go and stirring is maintained for 15 minutes. 1N hydrochloric acid is added until a pH of 2 is achieved. The dioxane is then evaporated off under reduced pressure and the aqueous solution is left in a refrigerator for 15 hours. The solid, filtered and dried in vacuo, yields the expected product.

Melting point: 210°–212° C. (toluene)

Step B: Methyl 5-(4-fluorobenzyl)-3-(3-nitrophenyl)-2-hydroxybenzoate 0.00081 mol of trimethylsilyldiazomethane is added dropwise to a solution of 0.0005 mol of the compound described in the preceding Step in a mixture of 1 ml of methanol and 4 ml of benzene. After 30 minutes' stirring, the solvents are evaporated off to yield the expected compound.

Elemental microanalysis:

|  | C% | H% | N% |
| --- | --- | --- | --- |
| calculated | 66.14 | 4.23 | 3.67 |
| found | 67.03 | 4.35 | 3.88 |

EXAMPLE 25

2-Furanyl-2-yl-[7-(3-nitrophenyl)benzo[b]furan-5-yl]methanone oxime

The expected product is obtained in accordance with the process described in Example 15 starting from the compound described in Example 4.

Melting point: 223°–225 ° C.
Elemental microanalysis:

|  | C% | H% | N% |
| --- | --- | --- | --- |
| calculated | 65.52 | 3.47 | 8.04 |
| found | 65.19 | 3.66 | 7.94 |

EXAMPLE 26

7-(3-Acetylaminophenyl)-5-(4-fluorobenzyl)benzo[b]furan

The expected product is obtained in accordance with the process described in Example 2 by replacing the 3-nitrophenylboric acid in Step F with 3-acetylaminophenylboric acid.

EXAMPLE 27

5-(4-Fluorobenzyl)-7-(3-trifluoromethylphenyl)benzo[b]furan

The expected product is obtained in accordance with the process described in Example 2 by replacing the 3-nitrophenylboric acid in Step F with 3-trifluoromethylphenylboric acid.

EXAMPLE 28

5-(4-Fluorobenzyl)-7-(3,5-di(trifluoromethyl)phenyl)benzo[b]furan

The expected product is obtained in accordance with the process described in Example 2 by replacing the 3-nitrophenylboric acid in Step F with 3,5-di(trifluoromethyl)phenylboric acid.

EXAMPLE 29

7-(3-Nitrophenyl)-5-(2-thenoyl)benzo[b]furan

The expected product is obtained in accordance with the process described in Example 4 by replacing the 2-furoyl chloride in Step B with 2-thenoyl chloride.

EXAMPLE 30

5-Benzyl-1-methyl-7-(3-nitrophenyl)indole

The expected product is obtained in accordance with the process described in Example 18 starting from the compound described in Example 13.

Elemental microanalysis:

|  | C% | H% | N% |
|---|---|---|---|
| calculated | 77.17 | 5.30 | 8.18 |
| found | 77.21 | 5.47 | 7.97 |

EXAMPLE 31

3-(3,5-Di(trifluoromethyl)phenyl)-5-(4-fluorobenzyl)-2-hydroxybenzaldehyde

The expected product is obtained in accordance with the process described in Example 8 starting from the compound described in Example 28.

EXAMPLE 32

3-(3,5-Di(trifluoromethyl)phenyl)-5-(4-fluorobenzyl)-2-hydroxybenzaldehyde oxime The expected product is obtained in accordance with the process described in Example 15 starting from the compound described in Example 31.

Elemental microanalysis:

|  | C% | H% | N% |
|---|---|---|---|
| calculated | 57.78 | 3.09 | 3.06 |
| found | 58.76 | 3.75 | 3.08 |

EXAMPLE 33

7-(3-Nitrophenyl)-5-(4-pyridylmethyl)benzo[b]furan hydrochloride

The expected product is obtained in accordance with the process described in Example 1, by replacing the benzyl bromide in Step C with 4-pyridylmethyl bromide. The corresponding hydrochloride is obtained by the action of a titrated solution of hydrochloric acid in ethanol.

Melting point: 74°–78° C.

Elemental microanalysis:

|  | C% | H% | Cl% | N% |
|---|---|---|---|---|
| calculated | 65.49 | 4.12 | 9.67 | 7.64 |
| found | 65.06 | 4.63 | 10.03 | 7.40 |

EXAMPLE 34

2-Hydroxy-3-(3-nitrophenyl)-5-(4-pyridylmethyl)benzaldehyde

The expected product is obtained in accordance with the process described in Example 8 starting from the compound described in Example 33.

EXAMPLE 35

2-Hydroxy-3-(3-nitrophenyl)-5-(4-pyridylmethyl)benzaldehyde oxime hydrochloride

The expected product is obtained in accordance with the process described in Example 15 starting from the compound described in Example 34. The corresponding hydrochloride is obtained by the action of a titrated solution of hydrochloric acid in ethanol.

Melting point: 218°–220° C.

Elemental microanalysis:

|  | C% | H% | N% | Cl% |
|---|---|---|---|---|
| calculated | 58.05 | 4.16 | 10.69 | 10.82 |
| found | 57.27 | 4.19 | 10.34 | 10.42 |

EXAMPLE 36

2-Hydroxy-3-(3-nitrophenyl)-5-(4-pyridylmethyl)benzonitrile

The expected product is obtained in accordance with the process described in Example 21 starting from the compound described in Example 35.

Melting point: 225° C. Elemental microanalysis:

|  | C% | H% | N% |
|---|---|---|---|
| calculated | 68.88 | 3.95 | 12.68 |
| found | 67.99 | 4.27 | 12.27 |

EXAMPLE 37

5-(4-Fluorobenzyl)-2-methoxy-3-(3-nitrophenyl)benzaldehyde oxime

The expected product is obtained in accordance with the process described in Example 18 starting from the compound described in Example 16.

Elemental microanalysis:

|  | C% | H% | N% |
|---|---|---|---|
| calculated | 66.31 | 4.50 | 7.36 |
| found | 65.55 | 4.60 | 7.15 |

EXAMPLE 38

2,N-Dihydroxy-3'-nitro-5-(4-pyridylmethyl)biphenyl-3-carboxamidine

A solution of 0.0024 mol of hydroxylamine hydrochloride in 1.5 ml of water is added to a solution of 0.0012 mol of the compound described in Example 36 and 8 ml of ethanol. The reaction mixture is heated at 75° C. for 72 hours. After cooling and concentration, the residue is purified by chromatography on silica gel, using a dichloromethane/tetrahydrofuran mixture, 8/2, as eluant, to yield the expected compound.

Melting point: 185°–186° C.

Elemental microanalysis:

|  | C% | H% | N% |
|---|---|---|---|
| calculated | 62.63 | 4.43 | 15.38 |
| found | 63.74 | 5.06 | 15.73 |

EXAMPLE 39

N-Methyl)-5-(4-flourobenzyl)-2-hydroxy-3-(3-nitrophenyl)benzamide 15 mmol of thionyl chloride are added at 0° C. to a solution of 10 mmol of the compound described in Example 24, Step A, in 30 ml of dichloromethane. After 1 hour's stirring, 25 mmol of methylamine are added, and the reaction mixture is heated at reflux for 3 hours, cooled and concentrated. The residue is taken up in a water/dichloromethane mixture and extracted, and the organic phase is dried and concentrated to yield the expected compound.

Elemental microanalysis:

|  | C% | H% | N% |
|---|---|---|---|
| calculated | 66.31 | 4.50 | 7.36 |
| found | 66.97 | 4.93 | 7.19 |

EXAMPLE 40

5-(4-Fluorobenzyl)-2-hydroxy-3-(3-nitrophenyl) benzohydroxamic acid

The expected product is obtained in accordance with the process described in Example 39 by replacing the methylamine with hydroxylamine.

Elemental microanalysis:

|  | C% | H% | N% |
|---|---|---|---|
| calculated | 62.83 | 3.95 | 7.33 |
| found | 60.62 | 3.89 | 6.90 |

EXAMPLE 41

N-(2-Chloroethyl)-5-(4-fluorobenzyl)-3-(3-nitrophenyl)-2-hydroxybenzamide

The expected product is obtained in accordance with the process described in Example 39, by replacing the methylamine with ethanolarmine, in the presence of thionyl chloride.

Elemental microanalysis:

|  | C% | H% | N% | Hal% |
|---|---|---|---|---|
| calculated | 61.62 | 4.23 | 6.53 | 8.27 |
| found | 62.04 | 4.62 | 6.25 | 8.85 |

EXAMPLE 42

5-[(2-Chloro-4-pyridyl)carbonyl]-7-(3-nitrophenyl) benzo[b]furane

The expected product is obtained in accordance with the process described in Example 4 by replacing the 2-furoyl chloride in Step B with 2-chloroisonicotinoyl.

Elemental microanalysis:

|  | C% | H% | N% | Cl% |
|---|---|---|---|---|
| calculated | 63.42 | 2.93 | 7.40 | 9.36 |
| found | 63.53 | 2.96 | 7.42 | 9.39 |

EXAMPLE 43

5-[(2-Chloro-4-pyridyl)hydroxymethyl]-7-(3-nitrophenyl) benzo[b]furane 0.0061 mol of sodium borohydride is added to a solution of 0.00061 mol of the compound described in Example 42 in 6 ml of tetrahydrofuran. After 15 minutes, 3 ml of a 1N hydrochloric acid solution are added dropwise,. The mixture is then diluted with ethyl ether and extracted and the organic phase is dried and concentrated. The residue obtained is purified by chromatography on silica gel, using a dichloromethane/ethyl acetate mixture, 95/5, as eluant, to yield the expected compound.

Melting point: 178°–180° C.

Elemental microanalysis:

|  | C% | H% | N% | Cl% |
|---|---|---|---|---|
| calculated | 63.09 | 3.44 | 7.36 | 9.31 |
| found | 63.28 | 3.80 | 7.05 | 8.62 |

EXAMPLE 44

7-(3-Nitrophenyl)-5-[(2-thienyl)hydroxymethyl] benzo[b]furan

The expected product is obtained in accordance with the process described in Example 43 starting from the compound described in Example 29.

Elemental microanalysis:

|  | C% | H% | N% | S% |
|---|---|---|---|---|
| calculated | 64.95 | 3.73 | 3.99 | 9.13 |
| found | 65.60 | 3.88 | 3.94 | 8.84 |

EXAMPLE 45

7-(3-Nitrophenyl)-5-(2-thienylmethyl)benzo[b]furan

The expected product is obtained in accordance with the process described in Example 1 by replacing the benzyl bromide in Step C with 2-chloromethylthiophene.

Elemental microanalysis:

|  | C% | H% | N% | S% |
|---|---|---|---|---|
| calculated | 68.04 | 3.91 | 4.18 | 9.56 |
| found | 68.47 | 4.20 | 4.26 | 9.26 |

EXAMPLE 46

7-(3-Nitrophenyl)-5-(4-pyridylvinyl)benzo[b]furan chlorhydrate

The expected product is obtained in accordance with the process described in Example 7 by, in Step A, replacing the tetrakis(triphenylphosphine)palladium with palladium(II) acetate and the allytributyltin with 4-vinylpyridine. The corresponding hydrochloride is obtained by the action of a titrated solution of hydrochloric acid in ethanol.

Melting point: >250° C.

Elemental microanalysis:

|  | C% | H% | Cl% | N% |
|---|---|---|---|---|
| calculated | 66.58 | 3.99 | 9.36 | 7.39 |
| found | 66.16 | 4.24 | 8.97 | 7.27 |

EXAMPLE 47

2-Iodo-6-(3-nitrophenyl)-4-(4-pyridylmethyl)phenol
Step A: 2-Bromo-4-(4-pyridylmethyl)aniline A solution of 18.34 g (0.103 mol) of N-bromosuccinimide in 60 ml of dimethylformamide is added dropwise, shielded from light, to a solution of 20 g (0.1084 mol) of 4-(4-pyridylmethyl)aniline in 180 ml of dimethylformamide. After 1 hour, the solvent is evaporated off under reduced pressure and the solid is taken up in 200 ml of dichloromethane. The solution is subsequently washed with 100 ml of water and then with 100 ml of a saturated sodium chloride solution. After customary treatment of the organic phase, an oil is obtained which is taken up in 500 ml of diethyl ether, and the whole is left in a refrigerator for 2 days. After filtration, the expected product is obtained.

Melting point: 102°–104° C.

Step B: 2-(3-Nitrophenyl)-4-(4-pyridylmethyl)aniline

A solution of 25 g (0.095 mol) of the compound described in the preceding Step, 23.8 g (0.1426 mol) of 3-nitrophenylboric acid, 26.3 g (0.19 mol) of potassium carbonate and 3.9 g (0.00475 mol) of palladium complex in 320 ml of dimethylformamide is heated for 16 hours at 80° C. under an inert atmosphere. After returning to room temperature, the solution is diluted with 200 ml of dimethylformamide and then filtered over Celite. The filtrate is evaporated under reduced pressure and is then taken up in 300 ml of ethyl acetate. Customary treatment of the organic phase followed by purification by chromatography on a silica column (eluant: dichloromethane/methanol 97/3) allows the title product to be obtained.

Melting point: 133°–135° C.

Step C: 2-(3-Nitrophenyl)-4-(4-pyridylmethyl)phenol

A solution of 13.7 g (0.045 mol) of the compound described in the preceding Step and 47 ml of 35% sulphuric acid is cooled to 0° C. The pyridinium sulphate is diluted with 50 ml of water and maintained at 0° C. A solution of 4.06 g (0.058 mol) of sodium nitrite and 50 ml of water is then added dropwise and under the surface while maintaining a temperature of less than +5° C. in the reactor. After 15 minutes' stirring at 0° C., the diazonium salt solution is added dropwise to a boiling solution of 25 ml of 35% sulphuric acid (the temperature of the reaction mixture always having to be higher than 70° C.). Once the addition is complete, the boiling solution is poured into 80 ml of an ice-cold concentrated (28%) ammonium hydroxide solution. The aqueous basic phase is extracted with dichloromethane containing 5% methanol. Customary treatment of the organic phase followed by purification by chromatography on a silica column (eluant: dichloromethane/methanol: 95/5) allows the expected product to be obtained.

Melting point: 122°–124° C.

Step D: 2-Iodo-6-(3-nitrophenyl)-4-(4-pyridylmethyl) phenol

To a solution of 0.026 mol of the compound described in the preceding Step in 675 ml of a 2/1 mixture of dichloromethane/methanol there are added, in one go, 0.0654 mol of sodium hydrogen carbonate and then 0.03 mol of benzyltrimethylammonium dichloroiodate. After 2 hours, the mixture is filtered and then evaporated. The solid is taken up in 100 ml of dichloromethane and washed twice with 50 ml of a 5% sodium hydrogen carbonate solution each time. Customary treatment of the organic phase followed by purification by chromatography on silica gel allows the title product to be obtained.

Melting point: 168°–170° C.

Elemental microanalysis:

|  | C% | H% | N% | I% |
|---|---|---|---|---|
| calculated | 50.02 | 3.03 | 6.48 | 29.36 |
| found | 49.64 | 3.32 | 6.22 | 28.94 |

EXAMPLE 48

2-Hydroxy-3-(3-nitrophenyl)-5-(4-pyridylmethyl) acetophenone hydrochloride

A solution of 0.0046 mol of the compound described in Example 47, 0.009 mol of ethoxyvinyltributyltin, 0.028 mol of lithium chloride and 0.0005 mol of tetrakis (triphenylphosphine)palladium(0) in 40 ml of tetrahydrofuran is heated at 65° C. for 76 hours. After cooling, the mixture is diluted with ethyl acetate and extracted. The organic phase is dried, concentrated and purified, using a dichloromethane/ethyl acetate mixture, 7/3, as eluant, to yield the expected compound. The corresponding hydrochloride is obtained by the action of a titrated solution of hydrochloric acid in ethanol.

Melting point: 219°–221° C.

Elemental microanalysis:

|  | C% | H% | N% | Cl% |
|---|---|---|---|---|
| calculated | 62.42 | 4.45 | 7.28 | 9.21 |
| found | 61.93 | 4.30 | 7.05 | 9.19 |

EXAMPLE 49

2-Hydroxy-3-(3-nitrophenyl)-5-(4-pyridylmethyl) acetophenone oxime

The expected product is obtained in accordance with the process described in Example 15 starting from the compound described in Example 48.

Melting point: 209°–211° C.

Elemental microanalysis:

|  | C% | H% | N% |
|---|---|---|---|
| calculated | 66.11 | 4.72 | 11.56 |
| found | 66.15 | 5.03 | 10.89 |

EXAMPLE 50

7-(3-Chlorophenyl)-5-(4-pyridylmethyl)benzo[b] furan

The expected product is obtained in accordance with the process described in Example 33 by replacing the 3-nitrophenylboric acid with 3-chlorophenylboric acid.

EXAMPLE 51

3-(3-Chlorophenyl)-2-hydroxy-5-(4-pyridylmethyl) benzaldehyde

The expected product is obtained in accordance with the process described in Example 8 starting from the compound described in Example 50.

EXAMPLE 52

3-(3-Chlorophenyl)-2-hydroxy-5-(4-pyridylmethyl) benzaldehyde oxime

The expected product is obtained in accordance with the process described in Example 15 starting from the compound described in Example 51.

Melting point: 124°–125° C.
Elemental microanalysis:

|  | C% | H% | Cl% | N% |
|---|---|---|---|---|
| calculated | 60.81 | 4.30 | 9.45 | 7.47 |
| found | 61.39 | 4.60 | 9.67 | 7.36 |

EXAMPLE 53

5-Benzyl-2-hydroxy-3-(3-nitrophenyl)benzaldehyde hydrazone

A solution of 0.006 mol of the compound described in Example 8 and 0.012 mol of hydrazine in 20 ml of toluene is heated at reflux for 30 minutes. After cooling, the expected product precipitates and is filtered and then dried.

Elemental microanalysis:

|  | C% | H% | N% |
|---|---|---|---|
| calculated | 69.15 | 4.93 | 12.10 |
| found | 69.45 | 5.16 | 11.64 |

EXAMPLE 54

7-(3-Nitrophenyl)-5-(4-pyridylthio)benzo[b]furan

Step A: 7-Methoxy-5-(4-pyridylthio)benzo[b]furan

A solution of 0.044 mol of the compound described in Example 1, Step B, 0.046 mol of 4-mercaptopyridine, 0.088 mol of sodium tert-butanolate and 0.0017 mol of tetrakis-(triphenylphosphine)palladium(0) in 180 ml of n-butanol is heated at 105° C. for 6 hours. After cooling, the reaction mixture is concentrated and the residue is purified by chromatography on silica gel, using a dichloromethane/ethyl acetate mixture, 8/2, as eluant, to yield the expected compound.

Melting point: 81°–83° C.

Step B: 7-Hydroxy-5-(4-pyridylthio)benzo[b]furan

The expected product is obtained in accordance with the process described in Example 1, Step D, starting from the compound described in the above Step.

Melting point: 154°–156° C.

Step C: 5-(4-Pyridylthio)-7-trifluoromethanesulphonyloxybenzo[b]furan

The expected product is obtained in accordance with the process described in Example 1, Step E, starting from the compound described in the above Step.

Step D: 7-(3-Nitrophenyl)-5-(4-pyridylthio)benzo[b]furan

The expected product is obtained in accordance with the process described in Example 1, Step F, starting from the compound described in the above Step.

Melting point: 135°–137° C.

Elemental microanalysis:

|  | C% | H% | N% | Cl% |
|---|---|---|---|---|
| calculated | 65.51 | 3.47 | 8.04 | 9.20 |
| found | 65.68 | 3.63 | 7.90 | 8.75 |

EXAMPLE 55

4-Benzyl-2-(but-1-enyl)-6-(3-nitrophenyl)phenol

A solution of 9 ml of 1.6M n-butyllithium in hexane is added dropwise, at 4° C., to a solution of 0.014 mol of n-propyltriphenylphosphonium bromide in 25 ml of tetrahydrofuran. After 30 minutes at 4° C. then 30 minutes at 20° C., a solution of 0.0048 mol of the compound described in Example 8 in 5 ml of tetrahydrofuran is added dropwise. The reaction mixture is then acidified with 15 ml of a 1N hydrochloric acid solution, diluted with ether and extracted. The organic phase is concentrated and purified by chromatography on silica gel, using a dichloro-methane/heptane mixture, 6/4, as eluant, to yield the expected compound.

Elemental microanalysis:

|  | C% | H% | N% |
|---|---|---|---|
| calculated | 76.86 | 5.89 | 3.90 |
| found | 76.53 | 6.06 | 3.91 |

Using the process described in Example 55 and replacing the n-propyltriphenylphosphonium bromide with the corresponding triphenylphosphonium halide, the compounds of Examples 56 and 57 are obtained.

EXAMPLE 56

4-Benzyl-2-(2-methoxyvinyl)-6-(3-nitrophenyl)phenol

Elemental microanalysis:

|  | C% | H% | N% |
|---|---|---|---|
| calculated | 73.12 | 5.30 | 3.88 |
| found | 73.31 | 5.14 | 4.40 |

EXAMPLE 57

4-Benzyl-2-(2-methylthiovinyl)-6-(3-nitrophenyl)phenol

Elemental microanalysis:

|  | C% | H% | N% | S% |
|---|---|---|---|---|
| calculated | 70.01 | 5.07 | 3.71 | 8.49 |
| found | 69.86 | 5.14 | 3.70 | 8.13 |

Using the processes described above, the following compounds are obtained:

EXAMPLE 58
2-(2-Methoxyvinyl)-6-(3-nitrophenyl)-5-(4-pyridylmethyl)phenol

EXAMPLE 59
7-(3-Nitrophenyl)-5-(4-pyridylmethyl)benzo[b]thiophene

EXAMPLE 60
2-Mercapto-3-(3-nitrophenyl)-5-(4-pyridylmethyl)benzaldehyde oxime

EXAMPLE 61
2-Methylthio-3-(3-nitrophenyl)-5-(4-pyridylmethyl)benzaldehyde oxime

EXAMPLE 62
5-(1H-2-Imidazolylmethyl)-7-(3-nitrophenyl)benzo[b]furan

EXAMPLE 63
2-Hydroxy-5-(1H-2-imidazolylmethyl)-3-(3-nitrophenyl)benzaldehyde oxime

EXAMPLE 64
5-[(1-Methyl-2-imidazolyl)methyl]-7-(3-nitrophenyl)benzo[b]furan

EXAMPLE 65
2-Hydroxy-5-[(1-methyl-2-imidazolyl)methyl]3-(3-nitrophenyl)benzaldehyde oxime

EXAMPLE 66
5-[(1-Methyl-5-imidazolyl)methyl]-7-(3-nitrophenyl)benzo[b]furan

EXAMPLE 67
2-Hydroxy-5-[(1-methyl-5-imidazolyl)methyl]-3-(3-nitrophenyl)benzaldehyde oxime

EXAMPLE 68
5-[(1-Methyl-4-imidazolyl)methyl]-7-(3-nitrophenyl)benzo[b]furan

EXAMPLE 69
2-Hydroxy-5-[(1-methyl-4-imidazolyl)methyl]-3-(3-nitrophenyl)benzaldehyde oxime

EXAMPLE 70
7-(3-Nitrophenyl)-5-(1H-3-pyrazolylmethyl)benzo[b]furan

EXAMPLE 71
2-Hydroxy-3-(3-nitrophenyl)-5-(1H-3-pyrazolylmethyl)benzaldehyde oxime

EXAMPLE 72
5-[(2-Methyl-3-pyrazolyl)methyl]-7-(3-nitrophenyl)benzo[b]furan

EXAMPLE 73
2-Hydroxy-5-[(2-methyl-3-pyrazolyl)methyl]-3-(3-nitrophenyl) benzaldehyde oxime

EXAMPLE 74
7-(3-Nitrophenyl)-5-(2-quinolylmethyl)benzo[b]furan

EXAMPLE 75
2-Hydroxy-3-(3-nitrophenyl)-5-(2-quinolylmethyl)benzaldehyde oxime

EXAMPLE 76
7-(3-Nitrophenyl)-5-(3-quinolylmethyl)benzo[b]furan

EXAMPLE 77
2-Hydroxy-3-(3-nitrophenyl)-5-(3-quinolylmethyl)benzaldehyde oxime

EXAMPLE 78
7-(3-Nitrophenyl)-5-(2-pyrazinylmethyl)benzo[b]furan

EXAMPLE 79
2-Hydroxy-3-(3-nitrophenyl)-5-(2-pyrazinylmethyl)benzaldehyde oxime

EXAMPLE 80
7-(4-Pyridyl)-5-(4-pyridylmethyl)benzo[b]furan

EXAMPLE 81
2-Hydroxy-3-(4-pyridyl)-5-(4-pyridylmethyl)benzaldehyde oxime

EXAMPLE 82
7-(3-Pyridyl)-5-(4-pyridylmethyl)benzo[b]furan

EXAMPLE 83
2-Hydroxy-3-(3-pyridyl)-5-(4-pyridylmethyl)benzaldehyde oxime

EXAMPLE 84
7-(2-Pyridyl)-5-(4-pyridylmethyl)benzo[b]furan

EXAMPLE 85
2-Hydroxy-3-(2-pyridyl)-5-(4-pyridylmethyl)benzaldehyde oxime

EXAMPLE 86
7-(3-Nitrophenyl)-5-(3-pyridylmethyl)benzo[b]furan

EXAMPLE 87
2-Hydroxy-3-(3-nitrophenyl)-5-(3-pyridyimethyl)benzaldehyde oxime

EXAMPLE 88
7-(3-Nitrophenyl)-5-(2-pyridylmethyl)benzo[b]furan

EXAMPLE 89
2-Hydroxy-3-(3-nitrophenyl)-5-(2-pyridylmethyl)benzaldehyde oxime

EXAMPLE 90
7-(3-Nitrophenyl)-5-[2-(4-pyridyl)ethyl]benzo[b]furan

EXAMPLE 91
2-Hydroxy-3-(3-nitrophenyl)-5-[2-(4-pyridyl)ethyl]benzaldehyde oxime

EXAMPLE 92
7-(3-Nitrophenyl)-5-phenoxybenzo[b]furan

EXAMPLE 93
2-Hydroxy-3-(3-nitrophenyl)-5-phenoxybenzaldehyde oxime

EXAMPLE 94
7-(3-Nitrophenyl)-5-(4-pyridyloxy)benzo[b]furan

EXAMPLE 95
2-Hydroxy-3-(3-nitrophenyl)-5-(4-pyridyloxy)benzaldehyde oxime

EXAMPLE 96
2-Acetylamino-4-benzyl-6-(3-nitrophenyl)phenol

EXAMPLE 97
4-Benzyl-2-formamido-6-(3-nitrophenyl)phenol

EXAMPLE 98
2-Acetylamino-4-(4-pyridylmethyl)-6-(3-nitrophenyl)phenol

EXAMPLE 99
2-Formamido-4-(4-pyridylmethyl)-6-(3-nitrophenyl)phenol

EXAMPLE 100
N-Methyl-5-benzyl-2-hydroxy-3-(3-nitrophenyl)benzaldehyde hydrazone Melting point: 154°–158° C.

Pharmacological study of the compounds of the invention

EXAMPLE 101

Measurement of the PDE activity

U937 cells are cultivated in a culture medium (RPMI) containing 10% foetal calf serum. Briefly, the cells are lysed and then centrifuged (100,000 g, 60 min., 4° C.) and the supernatant is recovered in order to separate the different forms of PDE by HPLC (C. LUGNIER and V. B. SCHINI, Biochem. Pharmacol., vol. 39, p.75–84, 1990). The PDE activity is measured by the appearance of [$^3$H]5' AMP resulting from the hydrolysis of cyclic [$^3$H]AMP. The PDE and the cyclic [$^3$H]AMP (1 μCi/ml) are incubated at 30° C. for 30 minutes. The radioactivity is measured using a liquid scintillation counter (Beckman LS 1701).

PDE IV is characterised by:

hydrolysis of cyclic AMP the absence of inhibition by cyclic GMP of the hydrolysis of cyclic AMP inhibition by rolipram, the reference compound.

The compounds are studied at two concentrations ($10^{-7}$M and $10^{-5}$M), in duplicate. The results are expressed as % inhibition of the phosphodiesterase activity. The better compounds of the present invention demonstrate an inhibition at $10^{-7}$M equal to or greater than 80%.

EXAMPLE 102

Pharmaceutical composition

| Formulation for the preparation of 1000 tablets each containing 100 mg of active ingredient | |
|---|---|
| compound of Example 15 | 10 g |
| hydroxypropyl cellulose | 2 g |
| wheat starch | 10 g |
| lactose | 100 g |
| magnesium stearate | 3 g |
| talc | 3 g |

We claim:

1. A Compound selected from those of formula (I)

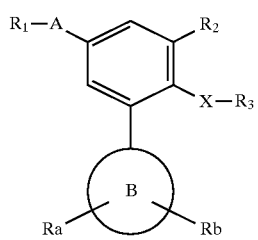

wherein:

$R_1$ represents substituted or unsubstituted ($C_3$–$C_7$)-cycloalkyl, substituted or unsubstituted phenyl, substituted or unsubstituted naphthyl, a saturated or unsaturated substituted or unsubstituted mono- or bi-cyclic heterocyclic group containing 1 to 3 hetero atoms inclusive selected from nitrogen, oxygen, and sulphur, a linear or branched substituted or unsubstituted ($C_1$–$C_6$)-alkyl, or a linear or branched substituted or unsubstituted ($C_1$$C_6$)-alkenyl;

A represents a bond (with the proviso that in that case $R_1$ is other than $C_1$- or $C_2$-alkyl), oxygen, sulphur, a group

a group,

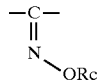

or a group

(wherein Rc represents hydrogen, linear or branched ($C_1$–$C_6$)-alkyl, or ($C_3$–$C_7$)-cycloalkyl), $R_2$ represents halogen, linear or branched substituted or unsubstituted ($C_1$–$C_6$)-alkyl, linear or branched ($C_1$–$C_6$) alkylcarbonyl, a linear or branched substituted or unsubstituted ($C_1$–$C_6$)-alkenyl, a linear or branched substituted or unsubstituted ($C_1$–$C_6$)-alkynyl, substituted or unsubstituted ($C_3$–$C_7$)-cycloalkyl, ($C_3$–$C_7$)-cycloalkylcarbonyl, formyl, carboxy, linear or branched ($C_1$–$C_6$)-alkoxycarbonyl, ($C_3$–$C_7$)-cycloalkyloxycarbonyl, carbamoyl (optionally substituted by one or two groups selected from linear or branched ($C_1$–$C_6$)-alkyl, ($C_3$–$C_7$)-cycloalkyl, hydroxy, linear or branched ($C_1$–$C_6$)-alkoxy, and ($C_3$–$C_7$)-cycloalkoxy, or forming together with the nitrogen atom of the carbamoyl carrying them a 5 to 7 member ring containing 1 to 3 heteroatoms selected from nitrogen, oxygen, and sulfur), amino (optionally substituted by one or two groups selected from linear or branched ($C_1$–$C_6$)-alkyl, linear or branched ($C_1$–$C_6$)-acyl, and ($C_3$–$C_7$)-cycloalkyl, or forming together with the nitrogen atom of the amino carrying them a 5 to 7 member ring containing 1 to 3 heteroatoms selected from nitrogen, oxygen, and sulfur), formylamino, cyano, amidino (optionally substituted by one or two groups selected from linear or branched ($C_1$–$C_6$)-alkyl and ($C_3$–$C_7$)-cycloalkyl, or forming together with the nitrogen atom of the amidino carrying them a 5 to 7 member ring containing 1 to 3 heteroatoms selected from nitrogen, oxygen, and sulfur), hydroxyaminomethyl (optionally substituted, independently on the nitrogen or oxygen, by linear or branched ($C_1$–$C_6$)-alkyl, ($C_3$–$C_7$)-cycloalkyl, or linear or branched ($C_1$–$C_6$)-acyl), amnide oxime (optionally substituted, independently on the nitrogen or oxygen, by linear or branched ($C_1$–$C_6$)-alkyl or ($C_3$–$C_7$)-cycloalkyl, or forming together with the nitrogen atom carrying them a 5 to 7 member ring containing 1 to 3 heteroatoms selected from nitrogen, oxygen, and sulfur), hydrazono (optionally substituted by one or two groups selected from linear or branched ($C_1$–$C_6$)-alkyl and ($C_3$–$C_7$)-cycloalkyl, or forming together with the nitrogen atom carrying them a 5 to 7 member ring containing 1 to 3 heteroatoms selected from nitrogen, oxygen, and sulfur), or a group selected from:

$$-\underset{\underset{R_{21}}{|}}{C}=N-O-R_{22} \quad \text{and} \quad -\underset{\underset{R_{21}}{|}}{C}=N(O)R_{23}$$

wherein:
$R_{21}$ represents hydrogen, linear or branched ($C_1$–$C_6$)-alkyl, or ($C_3$–$C_7$)-cycloalkyl,
$R_{22}$ represents hydrogen, linear or branched ($C_1$–$C_6$)-alkyl, ($C_3$–$C_7$)-cycloalkyl, or linear or branched ($C_1$–$C_6$)-acyl,
$R_{23}$ represents linear or branched ($C_1$–$C_6$)-alkyl or ($C_3$–$C_7$)-cycloalkyl,
$R_3$ represents hydrogen, linear or branched ($C_1$–$C_6$)-alkyl, ($C_3$–$C_7$)-cycloalkyl, or linear or branched ($C_1$–$C_6$)-acyl, or

[structure with $R_2$ and $X-R_3$]

together form the ring

[ring structure with X]

wherein
X represents oxygen, sulphur or NR" (in which R" represents hydrogen, linear or branched ($C_1$–$C_6$)-alkyl, ($C_3$–$C_7$)-cycloalkyl, or linear or branched ($C_1$–$C_6$)-acyl),
the ring B is phenyl,
Ra and Rb, which may be identical or different, each represents hydrogen, halogen, linear or branched ($C_1$–$C_6$)-alkyl, hydroxy, linear or branched ($C_1$–$C_6$)-alkoxy, carboxy, linear or branched ($C_1$–$C_6$)-polyhalogenoalkyl, cyano, nitro, linear or branched ($C_1$–$C_6$)-alkoxycarbonyl, ($C_3$–$C_7$)-cycloalkyloxycarbonyl, amino (optionally substituted by one or two linear or branched ($C_1$$C_6$)-alkyl, linear or branched ($C_1$$C_6$)-acyl, or ($C_3$–$C_7$)-cycloalkyl), ($C_3$–$C_7$)-cycloalkyl, or linear or branched ($C_1$–$C_6$)-alkoxy), sulfo, linear or branched ($C_1$–$C_6$)-alkylsulfonyl, or aminosulfonyl (optionally substituted by one on two linear or branched ($C_1$–$C_6$)-alkyl or ($C_3$–$C_7$)-cycloalkyl),
with the proviso that
when A represents a bond or oxygen, B represents phenyl, $R_1$ represents substituted or unsubstituted ($C_3$–$C_7$)-cycloalkyl, substituted or unsubstituted phenyl, or substituted or unsubstituted naphthyl, X represents oxygen or NR" (in which R" represents hydrogen or linear or branched ($C_1$–$C_6$)-alkyl) and $R_3$ represents hydrogen or linear or branched ($C_1$–$C_6$)-alkyl, then $R_2$ is other than carboxy,
their isomers and the addition salts thereof with a pharmaceutically-acceptable acid or base.

2. A compound of claim 1 wherein X represents oxygen.

3. A compound of claim 1 wherein $R_1$ represents alkyl substituted by substituted or unsubstituted phenyl.

4. A compound of claim 1 wherein $R_1$ represents alkyl substituted by a saturated or unsaturated substituted or unsubstituted heterocyclic group containing 1 to 3 hetero atoms selected from oxygen, nitrogen, and sulphur.

5. A compound of claim 4 wherein $R_1$ represents alkyl substituted by substituted or unsubstituted pyridyl.

6. A compound of claim 4 wherein $R_1$ represents a saturated or unsaturated substituted or unsubstituted heterocyclic group containing 1 to 3 hetero atoms selected from oxygen, nitrogen, and sulphur.

7. A compound of claim 1 wherein $R_2$ represents halogen, linear or branched substituted or unsubstituted ($C_1$–$C_6$)-alkyl, linear or branched ($C_1$–$C_6$) alkylcarbonyl, linear or branched substituted or unsubstituted ($C_1$–$C_6$)-alkenyl, linear or branched substituted or unsubstituted ($C_1$–$C_6$)-alkynyl, substituted or unsubstituted ($C_3$–$C_7$)-cycloalkyl, ($C_3$–$C_7$)-cycloalkylcarbonyl, formyl, carboxy, linear or branched ($C_1$–$C_6$)-alkoxycarbonyl, ($C_3$–$C_7$)-cycloalkyloxycarbonyl, carbamoyl (optionally substituted by one or two groups selected from linear or branched ($C_1$–$C_6$)-alkyl, ($C_3$–$C_7$)-cycloalkyl, hydroxy, linear or branched ($C_1$–$C_6$)-alkoxy, and ($C_3$–$C_7$)-cycloalkoxy, or forming together with the nitrogen atom carrying them a 5 to 7 member ring containing 1 to 3 heteroatoms selected from nitrogen, oxygen, and sulfur), amino (optionally substituted by one or two groups selected from linear or branched ($C_1$–$C_6$)-alkyl, linear or branched ($C_1$–$C_6$)-acyl, and ($C_3$–$C_7$)-cycloalkyl, or forming together with the nitrogen atom carrying them a 5 to 7 member ring containing 1 to 3 heteroatoms selected from nitrogen, oxygen, and sulfur), formylamino, cyano, amidino (optionally substituted by one or two groups selected from linear or branched ($C_1$–$C_6$)-alkyl and ($C_3$–$C_7$)-cycloalkyl, or forming together with the nitrogen atom carrying them a 5 to 7 member ring containing 1 to 3 heteroatoms selected from nitrogen, oxygen, and sulfur), hydroxyaminomethyl (optionally substituted, independently on the nitrogen or oxygen, by linear or branched ($C_1$–$C_6$)-alkyl, ($C_3$–$C_7$)-cycloalkyl, or linear or branched ($C_1$–$C_6$)-acyl), amide oxime (optionally substituted, independently on the nitrogen or oxygen, by linear or branched ($C_1$–$C_6$)-alkyl or ($C_3$–$C_7$)-cycloalkyl, or forming together with the nitrogen atom carrying them a 5 to 7 member ring containing from 1 to 3 heteroatoms selected nitrogen, oxygen, and sulfur), hydrazono (optionally substituted by one or two groups selected from linear or branched ($C_1$–$C_6$)-alkyl and ($C_3$–$C_7$)-cycloalkyl, or forming together with the nitrogen atom carrying them a 5 to 7 member ring containing 1 to 3 heteroatoms selected from nitrogen, oxygen or sulfur), or a group selected from:

$$-\underset{\underset{R_{21}}{|}}{C}=N-O-R_{22} \quad \text{and} \quad -\underset{\underset{R_{21}}{|}}{C}=N(O)R_{23}$$

wherein:
$R_{21}$ represents hydrogen, linear or branched ($C_1$–$C_6$)-alkyl, or ($C_3$–$C_7$)-cycloalkyl,
$R_{22}$ represents hydrogen, linear or branched ($C_1$–$C_6$)-alkyl, ($C_3$–$C_7$)-cycloalkyl, or linear or branched ($C_1$–$C_6$)-acyl, and
$R_{23}$ represents linear or branched ($C_1$–$C_6$)-alkyl or ($C_3$–$C_7$)-cycloalkyl.

8. A compound of claim 1, wherein

[structure with $R_2$ and $X-R_3$]

together form the ring

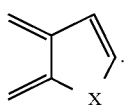

9. A compound of claim 8, wherein X represents oxygen.

10. A compound of claim 1, which is 5-benzyl-2-hydroxy-3-(3-nitrophenyl)benzaldehyde oxime, its isomers and also the addition salts thereof with a pharmaceutically-acceptable base.

11. A method for treating a living body afflicted with a condition requiring a group IV phosphodiesterase inhibitor comprising the step of administering to the living body an amount of a compound of claim 1 which is effective for alleviation of said condition.

12. A pharmaceutical composition useful as group IV phosphodie sterase inhibitor comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,877,190
DATED : Mar. 2, 1999
INVENTOR(S) : A. Dhainaut, G. Poissonet, E. Canet, M. Lonchampt Page 1 of 3

It is certified that error appears in the above-identified patent and that said Letters Patent is hereby corrected as shown below:

Title Page, [75] Inventors: "Emmanuel Canft" should read -- Emmanuel Canet --.

Column 2, line 16: "Exp. Inmunol.," should read -- Exp. Immunol., --.

Column 12, line 46: In the formula, at the top right, the "O" should read -- N --.

Column 12, line 65: "Ra" in the formula should read -- Re --.

Column 13, line 2: At the right hand side of the formula, insert -- (I/s) --. (This is the number of the formula.)

Column 16, line 38: "Step D: 5-(2-Furoyi)-" should read -- Step D: 5-(2-Furoyl)- --.

Column 16, line 66: "7-mnethoxybenzo[b]furan," should read -- 7-methoxybenzo[b]furan, --.

Column 24, line 19: "Elemental microanalysis:" should begin line 20.

Column 25, line 37: "ethanolarmine," should read -- ethanolamine --.

Column 32, line 67: This line should be moved to the top of Column 33.

UNITED STATES PATENT AND TRADEMARK OFFICE
CERTIFICATE OF CORRECTION

PATENT NO. : 5,877,190
DATED : Mar. 2, 1999
INVENTOR(S) : A. Dhainaut, G. Poissonet, E. Canet, M. Lonchampt Page 2 of 3

It is certified that error appears in the above-identified patent and that said Letters Patent is hereby corrected as shown below:

Column 33, line 65: "$(C_1C_6)$-alkenyl;" should read -- $(C_1-C_6)$-alkenyl; --.

Column 34, line 8(approx.): Insert a -- , -- (comma) after the formula and before "or". Preliminary Amendment dtd 10/3/97, Column 34, line 15: Delete the "," (comma) after the formula in this line and before "wherein".

Column 34, line 55: "amnide" should read -- amide --.

Column 35, line 43 & 44: In both instances, "$(C_1C_6)$-" should read -- $(C_1-C_6)$- --.

Column 35, line 44: Between "-cycloalkyl)," and "$(C_3-C_7)$" at the end of the line, insert the following: -- carbamoyl (optionally substituted by one or two linear or branched $(C_1-C_6)$-alkyl, --.

Column 36, line 40: Delete the word "from". Page 4 of the Preliminary Amendment dtd 10/3/97, Column 36, line 41: Insert -- from -- between "selected" and "nitrogen" at the beginning of the line.

UNITED STATES PATENT AND TRADEMARK OFFICE
CERTIFICATE OF CORRECTION

PATENT NO. : 5,877,190
DATED : Mar. 2, 1999
INVENTOR(S) : A. Dhainaut, G. Poissonet, E. Canet, M. Lonchampt It is certified that error appears in the above-identified patent and that said Letters Patent is hereby corrected as shown below:

Column 36, line 46: Insert a comma -- , -- after the word "oxygen", and change "or" (first instance) to -- and --.
10/3/97, Column 38, line 7: "phosphodie sterase" should read -- phosphodiesterase --.
Amendment dtd 10/3/97, Signed and Sealed this Fifteenth Day of June, 1999

Attest:

Q. TODD DICKINSON

Attesting Officer

Acting Commissioner of Patents and Trademarks